(12) United States Patent
Yodfat et al.

(10) Patent No.: US 10,258,737 B2
(45) Date of Patent: Apr. 16, 2019

(54) ANALYTE MONITORING AND FLUID DISPENSING SYSTEM

(71) Applicant: Roche Diabetes Care, Inc., Indianapolis, IN (US)

(72) Inventors: Ofer Yodfat, Maccabim-Reut (IL); Ruthy Kaidar, Haifa (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 118 days.

(21) Appl. No.: 14/847,101

(22) Filed: Sep. 8, 2015

(65) Prior Publication Data

US 2015/0374905 A1 Dec. 31, 2015

Related U.S. Application Data

(63) Continuation of application No. 12/744,268, filed as application No. PCT/IL2008/001521 on Nov. 20, 2008, now abandoned.

(60) Provisional application No. 61/004,047, filed on Nov. 21, 2007.

(51) Int. Cl.
*A61M 5/142* (2006.01)
*A61M 5/172* (2006.01)

(52) U.S. Cl.
CPC ...... *A61M 5/14248* (2013.01); *A61M 5/1723* (2013.01); *A61M 2005/14268* (2013.01); *A61M 2005/1726* (2013.01); *A61M 2205/3592* (2013.01); *A61M 2205/50* (2013.01); *A61M 2205/8206* (2013.01); *A61M 2210/04* (2013.01); *A61M 2230/201* (2013.01)

(58) Field of Classification Search
CPC ...... A61M 5/1723; A61M 2005/14268; A61M 2005/1726; A61M 2230/201
See application file for complete search history.

(56) References Cited

U.S. PATENT DOCUMENTS

| 3,771,694 A | 11/1973 | Kaminski |
| 4,498,843 A | 2/1985 | Schneider et al. |
| 4,657,486 A | 4/1987 | Stempfle et al. |
| 4,694,832 A | 9/1987 | Ungerstedt |

(Continued)

FOREIGN PATENT DOCUMENTS

| WO | 2006108809 A1 | 10/2006 |
| WO | 2008029403 A1 | 3/2008 |

(Continued)

OTHER PUBLICATIONS

Amerov et al., "Scattering and Absorption Effects in the Determination of Glucose in White Blood by Near-Infrared Spectroscopy", Anal. Chem., vol. 77, pp. 4587-4594 (2005).

(Continued)

*Primary Examiner* — Emily L Schmidt
(74) *Attorney, Agent, or Firm* — Dinsmore & Shohl, LLP

(57) ABSTRACT

Disclosed is a skin adherable device for delivering therapeutic fluid into a body of a patient. The device includes a monitoring apparatus, a dispensing apparatus, and a tip for delivering the therapeutic fluid into the body of the patient and for monitoring bodily analyte in the body of the patient. The dispensing apparatus may continuously deliver the therapeutic fluid to the body of the patient and the monitoring apparatus may continuously monitor bodily analytes of the patient.

20 Claims, 34 Drawing Sheets

(56) References Cited

U.S. PATENT DOCUMENTS

| | | | |
|---|---|---|---|
| 5,957,895 A | 9/1999 | Sage et al. | |
| 6,091,976 A | 7/2000 | Pfeiffer et al. | |
| 6,360,888 B1 | 3/2002 | McIvor et al. | |
| 6,391,643 B1 | 5/2002 | Chen et al. | |
| 6,485,461 B1 | 11/2002 | Mason et al. | |
| 6,558,351 B1 | 5/2003 | Steil et al. | |
| 6,589,229 B1 | 7/2003 | Connelly et al. | |
| 6,723,072 B2 | 4/2004 | Flaherty et al. | |
| 6,740,059 B2 | 5/2004 | Flaherty | |
| 6,881,551 B2 | 4/2005 | Heller et al. | |
| 6,892,085 B2 | 5/2005 | McIvor et al. | |
| 2004/0092865 A1* | 5/2004 | Flaherty | A61M 5/14276 604/93.01 |
| 2004/0158207 A1* | 8/2004 | Hunn | A61M 5/158 604/164.01 |
| 2005/0119588 A1 | 6/2005 | Model et al. | |
| 2006/0224141 A1 | 10/2006 | Rush et al. | |
| 2006/0253085 A1 | 11/2006 | Geismar et al. | |
| 2006/0253086 A1 | 11/2006 | Moberg et al. | |
| 2007/0106218 A1 | 5/2007 | Yodfat et al. | |
| 2007/0191702 A1 | 8/2007 | Yodfat et al. | |
| 2008/0051697 A1 | 2/2008 | Mounce et al. | |
| 2008/0051714 A1* | 2/2008 | Moberg | A61M 5/1413 604/135 |
| 2008/0086042 A1 | 4/2008 | Brister et al. | |
| 2008/0097381 A1* | 4/2008 | Moberg | A61M 5/1413 604/506 |
| 2008/0119707 A1 | 5/2008 | Stafford | |
| 2008/0214916 A1 | 9/2008 | Yodfat et al. | |
| 2008/0215035 A1 | 9/2008 | Yodfat et al. | |
| 2008/0281290 A1 | 11/2008 | Yodfat et al. | |
| 2008/0319414 A1 | 12/2008 | Yodfat et al. | |
| 2008/0319416 A1 | 12/2008 | Yodfat et al. | |
| 2009/0062767 A1 | 3/2009 | Van Antwerp et al. | |
| 2010/0204657 A1 | 8/2010 | Yodfat et al. | |

FOREIGN PATENT DOCUMENTS

| | | |
|---|---|---|
| WO | 2008038274 A1 | 4/2008 |
| WO | 2008078319 A1 | 7/2008 |
| WO | 2009004627 A2 | 1/2009 |

OTHER PUBLICATIONS

Boizel, R., "Glocose monitoring and pump data management software operated on a personal digital assistant can contribute to improve diabetes control in CSII-treated patients", Diabetes Metab., vol. 33, pp. 314-315 (2007).

Hanlon et al., "Prospects for in vivo Raman spectroscopy", Physics Med. Biol., vol. 45, No. 2, pp. R1-R59 (2000).

Hoogma et al., "Comparison of the effects of continuous subcutaneous insulin infusion (CSII) and NPH-based multiple daily insulin injections (MDI) on glycaemic control and quality of life: results of the 5-nations trial", Diabetes Med., vol. 23, No. 2, pp. 141-147 (2007).

Khalil, O.S., "Non-Invasive Glucose Measurement Technologies: An Update from 1999 to the Dawn of the New Millennium", Diabetes Tech, Therapeutics, vol. 6, No. 5, pp. 660-697 (2004).

MacKenzie et al., "Advances in Photoacoustic Noninvasive Glucose Testing", Clin. Chem., vol. 45, No. 9, pp. 1587-1595 (1999).

Maran et al., "Continuous Subcutaneous Glucose Monitoring in Diabetec Patients", Diabetes Care, vol. 25, No. 2, pp. 347-352 (2002).

McCartney et al., "Near-Infrared fluorescence lifetime assay for serum glucose based on allophycocyanin-labeled concanavalin A", Anal. Biochem., vol. 292, pp. 216-221 (2001).

Parkner et al., "Overnight CSII as supplement to oral antidiabetic drugs in Type 2 diabetes", Diabetes Obes. Metab., vol. 19, pp. 557-563 (2007).

Rolinski et al., "A time resolved near-infrared fluorescence assay for glucose: opportunities for trans-dermal sensing", J. Photochem. Photobiol. B, vol. 54, pp. 26-34 (2000).

Tamada et al., "Noninvasive Glucose Monitoring Comprehensive Clinical Results", J. Am. Med. Assoc., vol. 282, No. 19, pp. 1839-1844 (1999).

International Search Report for PCT Application No. PCT/IL2008/001521, dated Mar. 20, 2009.

Written Opinion of the International Search Authority for PCT Application No. PCT/IL2008/001521, dated Mar. 20, 2009.

* cited by examiner

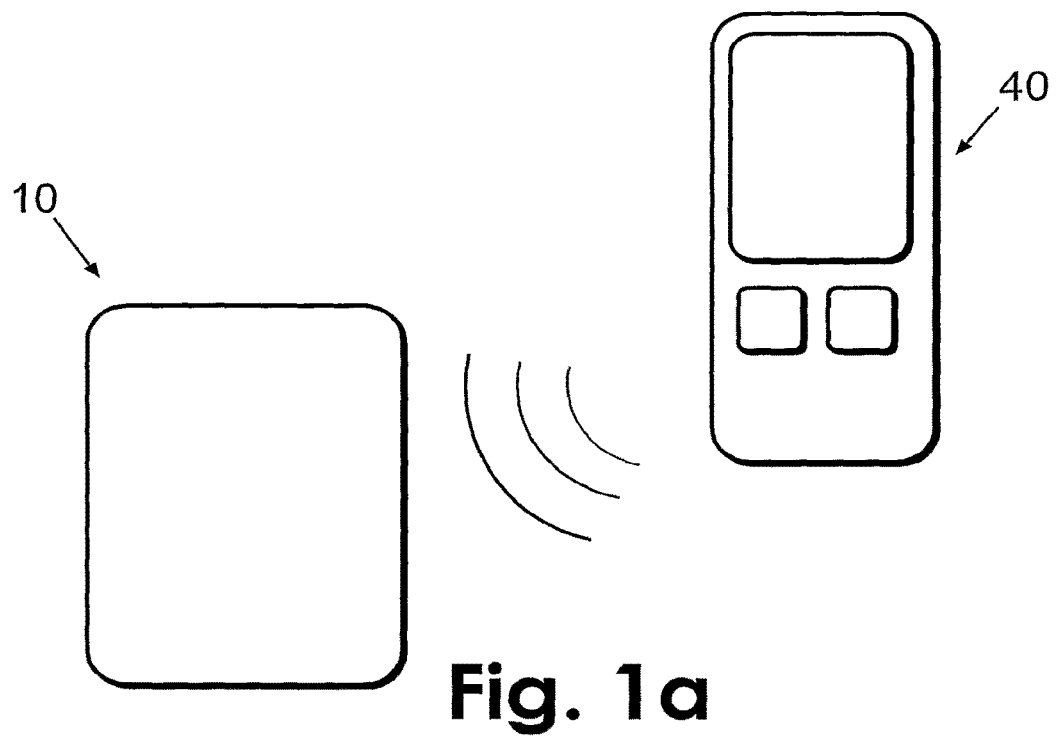
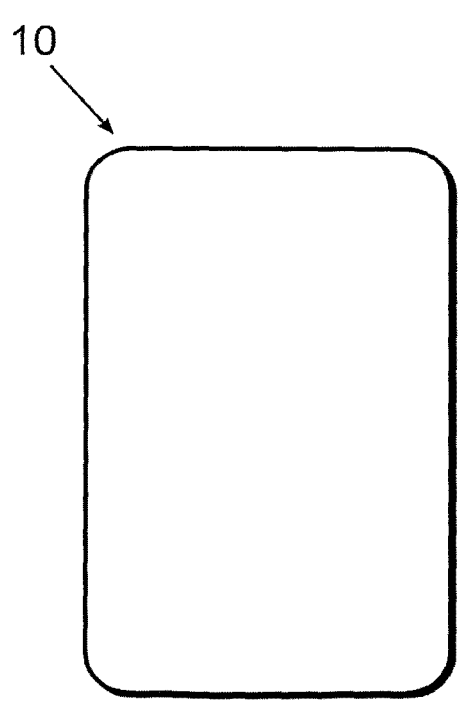
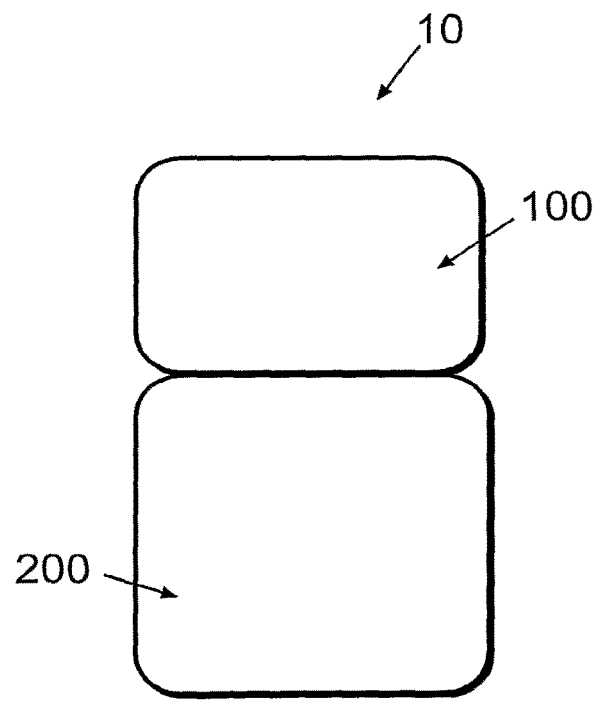
Fig. 1a
Fig. 1b
Fig. 1c

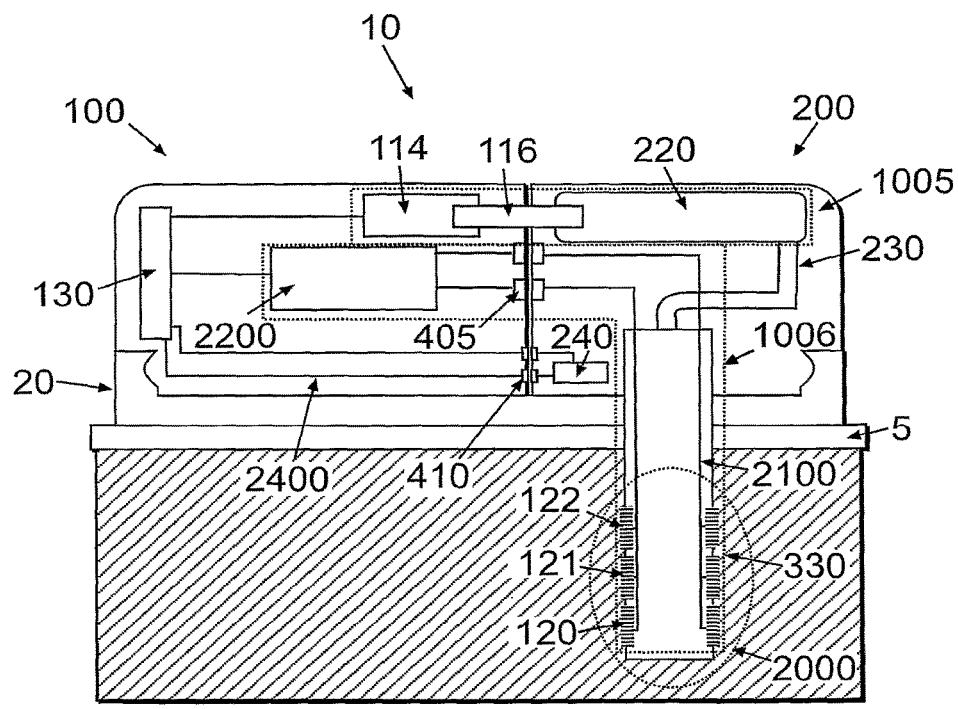
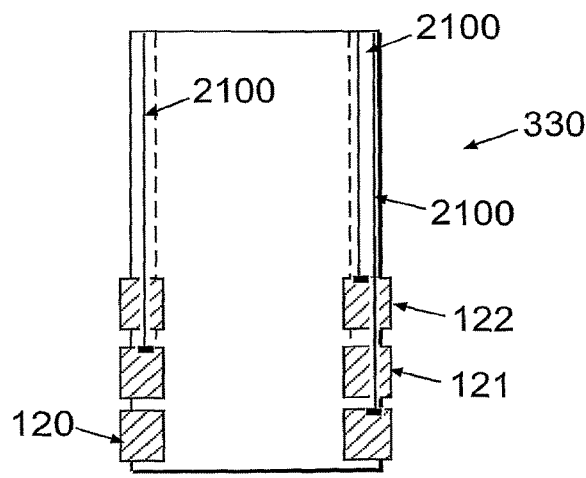
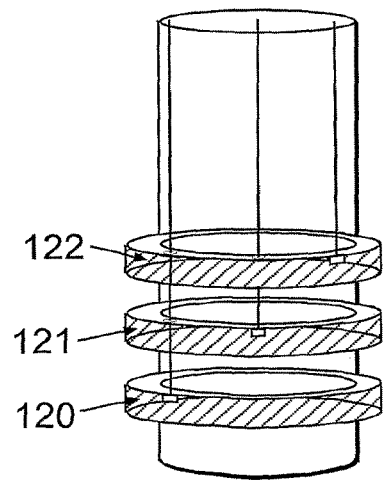
Fig. 13a
Fig. 13b
Fig. 13c

ANALYTE MONITORING AND FLUID DISPENSING SYSTEM

CROSS-REFERENCE TO RELATED APPLICATIONS

This application is a continuation application of U.S. patent application Ser. No. 12/744,268 filed May 21, 2010, which is a 35 U.S.C. § 371 national stage entry of PCT/IL2008/001521, which has an international filing date of 20 Nov. 2008, which claims priority to U.S. Provisional Patent Application No. 61/004,047, entitled "Analyte Monitoring and Fluid Dispensing System," filed on Nov. 21, 2007, the disclosure of which are incorporated herein by reference in their entireties.

FIELD

Systems, devices, and methods for continuous monitoring of bodily analyte and continuous dispensing of therapeutic fluid are described herein. More particularly, a system comprising a continuous glucose monitor and insulin dispenser is described herein. Even more particularly, a device that is configured as a miniature, portable, single unit that can be adhered to a patient's skin and connected to at least one subcutaneous tip to continuously monitor glucose levels and dispense insulin is described herein.

The systems, devices and methods are not limited strictly to delivering insulin and monitoring glucose but, rather, apply to delivering any other drug and concomitantly monitoring any analyte. When used in the following description the term "analyte" means any solute composed of specific molecules dissolved in an aqueous medium.

BACKGROUND

Continuous Subcutaneous Insulin Injection (SCII)

Medical treatment of several illnesses requires continuous drug infusion into various body compartments, such as subcutaneous and intra-venous injections. Diabetes mellitus (DM) patients, for example, require the administration of varying amounts of insulin throughout the day to control their glucose levels. In recent years, ambulatory portable insulin infusion pumps have emerged as a superior alternative to multiple daily syringe injections of insulin, initially for Type 1 diabetes patients (Diabetes Medicine 2006; 23(2):141-7) and consecutively for Type 2 diabetes patients (Diabetes Metab 2007 Apr. 30, Diabetes Obes Metab 2007 Jun. 26). These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal.

The first generation of portable infusion pumps concerns "pager-like" devices with a reservoir contained within the device's housing. These devices are provided with a long tube for delivering insulin from the pump attached to a patient's belt to a remote insertion site. Both basal and bolus volumes deliveries in these "pager-like" devices are controlled via a set of buttons provided on the device. A human interface screen is provided on the device housing for advising the user about fluid delivery status, for programming flow delivery, for alerts and alarms. Such devices are disclosed, for example, in U.S. Pat. Nos. 3,771,694, 4,657, 486 and 4,498,843. These devices represent a significant improvement over multiple daily injections, but nevertheless, they all suffer from several major drawbacks, among which are the large size and weight, long delivery tubing and lack of discreetness.

To avoid the consequences of a long delivery tube, a new concept on which a second generation pumps are based, was proposed. As described in prior art, the new concept concerns a remote controlled skin adherable device with a housing having a bottom surface adapted for contact with the patient's skin, a reservoir disposed within the housing, and an injection needle adapted for communication with the reservoir. In these devices, the user interface means is configured as a separate remote control unit that contains operating buttons and screen providing fluid delivery status, programming flow delivery, alerts and alarms, as described, for example, in U.S. Pat. Nos. 5,957,895, 6,589,229, 6,740,059, 6,723,072, and 6,485,461. These second generation devices also have several limitations, such as being heavy, bulky, and expensive because the device should be replaced every 2-3 days. Another major drawback of these second generation skin adherable devices is associated with the remote controlled drug administration. The user is totally dependent on the remote control unit and cannot initiate bolus delivery or operate the device if the remote control unit is not at hand, or it is lost or malfunctions (practically, this means that the patient cannot eat).

A third generation of skin adherable infusion devices was devised to avoid the price limitation and to extend patient customization. An example of such a device was described in copending/co-owned patent applications U.S. patent application Ser. No. 11/397,115 and International Patent Application No. PCT/IL06/001276. This third generation device contains a remote control unit and a skin adherable device/patch unit that can be comprised of two parts:

Reusable part—containing the metering portion, electronics, and other relatively expensive components.

Disposable part—containing the reservoir and in some embodiments batteries.

This concept provides a cost-effective, skin adherable infusion device and allows diverse usage such as various reservoir sizes, various needle and cannula types.

In a co-pending/co-owned International Application No. PCT/IL07/001578 and U.S. Patent Application No. PCT/IL07/001578 and U.S. patent application Ser. No. 12/004,837, claiming priority to U.S. Provisional Patent Application No. 60/876,679, a fourth generation patch unit that can be disconnected and reconnected from and to a skin adherable cradle unit was disclosed.

The fourth generation detachable skin adherable patch can be remotely controlled or can be operated by a dedicated control buttons that are located on the patch housing as disclosed in the co-owned/co-pending U.S. Provisional Patent Application No. 60/691,527 By virtue of the fourth generation patch the user can deliver a desired bolus dose by repetitive pressing of control buttons.

Continuous Glucose Monitoring (CGM)

Most diabetic patients currently measure their own glucose levels several times during the day by obtaining fingerprick capillary samples and applying the blood to a reagent strip for analysis in a portable meter. While glucose level self-monitoring has had a major impact on improving diabetes care in the last few decades, the disadvantages of this technology are substantial and consequently leading to non-compliance. Blood sampling is associated with the discomfort of multiple skin pricking, testing cannot be performed during sleeping and when the subject is occupied (e.g., during driving a motor vehicle), and intermittent testing may miss episodes of hyper- and hypoglycemia. The ideal glucose monitoring technology should therefore employ automatic and continuous testing.

Currently there are three techniques for continuously monitoring of glucose in the subcutaneous interstitial fluid (ISF):

1. The first technique is based on use of glucose oxidase based sensors as described in U.S. Pat. No. 6,360,888 to McIvor et al. and U.S. Pat. No. 6,892,085 to McIvor et al., both assigned to Medtronic MiniMed Inc. (CGMS, Guardian™ and CGMS Gold), and U.S. Pat. No. 6,881,551 to Heller et al., assigned to Abbott Laboratories, formerly TheraSense, Inc., (Navigator®). These sensors consist of a subcutaneously implantable, needle-type amperometric enzyme electrode, coupled with a portable logger.
2. The second technique is based on use of reverse iontophoresis-based sensors as detailed in U.S. Pat. No. 6,391,643 to Chen et al., assigned to Cygnus, Inc. (GlucoWatch™). A small current passed between two electrodes located on the skin surface draws ions and (by electro-endosmosis) glucose-containing interstitial fluid to the surface and into hydrogel pads incorporating a glucose oxidase biosensor (JAMA 1999; 282: 1839-1844).
3. The third commercial technology in current clinical use is based on microdialysis (Diab Care 2002; 25: 347-352), as detailed in U.S. Pat. No. 6,091,976 to Pfeiffer et al., assigned to Roche Diagnostics. There exists also marketable device (Menarini Diagnostics, Gluco-Day™). Here, a fine, hollow dialysis fiber is implanted in the subcutaneous tissue and perfused with isotonic fluid. Glucose from the tissue diffuses into the fiber and is pumped outside the body for measurement by a glucose oxidase based electrochemical sensor. Initial reports (Diab Care 2002; 25: 347-352) show good agreement between sensor and blood glucose readings, and good stability with a one-point calibration over one day.

Closed Loop Systems

In an artificial pancreas, sometimes referred to as a "closed loop" system, an insulin pump delivers appropriate dosage of insulin according to continuous glucose monitor readings. An artificial pancreas voids human interface and is expected to eliminate debilitating episodes of hypoglycemia, particularly nighttime hypoglycemia. An intermediate step in the way to achieve a "closed loop" system is an "open loop" (or "semi-closed loop") system also called "closed loop with meal announcement." In this model, user intervention is required, in a way similar to using of today's insulin pumps by keying in the desired insulin before they eat a meal. A closed loop system is discussed in U.S. Pat. No. 6,558,351 to Steil et al., assigned to Medtronic MiniMed. The system is comprised of two separate devices, a glucose monitor and an insulin pump which are adherable to two remotely body sites and the loop is closed by an RF communication link. This closed loop system has some major drawbacks:

1. The glucose monitor and insulin pump are two discrete components, thus there are required two insertion sites and two skin-pricking sites for every replacement of the insulin pump and the sensor, usually every 3 days.
2. Being separated apart, the two system components should be connected either by radio communication link or by wires.
3. The pump is heavy and bulky with long tubing making the system non-discreet.
4. The system is extremely expensive because the pump infusion set and the monitor sensor should be disposed every 3 days.

SUMMARY OF THE INVENTION

Systems, devices, and methods for continuous monitoring of bodily analyte and continuous dispensing of therapeutic fluid are provided. Some embodiments relate to a device that includes both a monitoring apparatus and a dispensing apparatus. The dispensing apparatus may be used for infusing fluid into the body and the monitoring apparatus may be used for monitoring analytes within the body. The monitoring apparatus and the dispensing apparatus can share a single subcutaneously insertable tip, designed to allow both the concomitantly monitoring of analyte levels and the dispensing of fluid. In some embodiments, the apparatus can have a plurality of insertable tips that can be connected to the monitoring and dispensing apparatuses to perform monitoring of analyte(s) and dispensing of fluid(s). The tip functions as a probe for monitoring analyte levels within the body, for example, within the interstitial fluid ("ISF") and at the same time as a cannula through which fluid is delivered to the body (hereinafter "tip"). The dispensing apparatus and the monitoring apparatus may work independently of each other, or may work together as a closed loop or semi-closed loop system. In some embodiments, the dispensing fluid is insulin to be used with diabetic patients and the analyte is glucose. The monitoring apparatus and dispensing apparatus may comprise a fluid delivery device, which may be configured as a skin adherable device (hereinafter "patch unit").

Some embodiments of the device include at least one of the following units and elements:

1. A patch unit that includes the monitoring apparatus and the dispensing apparatus. The monitoring apparatus includes sensing means and connecting wires; and, the dispensing apparatus includes a reservoir, driving mechanism, and pumping mechanism. The patch unit further includes a printed circuit board ("PCB"), which includes a processor and can include a transceiver. The processor controls operation of the dispensing and monitoring apparatuses (hereinafter "processor-controller"). For programming and data presentation, the device can be provided with a remote control unit and/or with one or more operating buttons on the patch unit. The device further can be provided with a skin adherable cradle unit. The patch unit can be connected or disconnected to the cradle unit. The dispensing apparatus of the patch unit may employ different dispensing mechanisms, such as a syringe with a propelling plunger/piston (syringe type) mechanism or a peristaltic mechanism. The patch unit further includes a reservoir and an outlet port which allows fluid communication between the reservoir and the tip when the patch unit is connected to the cradle unit. The patch unit may be configured as a single part or consist of two parts, which include:
    a. A reusable part—contains relatively expensive components, e.g., pumping mechanism, electronics.
    b. A disposable part—contains relatively non-expensive and disposable components, e.g., reservoir.

The patch unit further includes a power source which can be contained either in the reusable part or in the disposable part.
2. A cradle unit, which is provided with a flat bottom covered by a sheet with an adhesive for adhering the cradle unit to the skin, with a passageway (hereinafter "well") and at least one anchors for the tip. The cradle unit further includes at least one connector, e.g., latches for connection and disconnection of the patch unit to and from the cradle unit.

3. A cartridge unit—includes the following:
   a. A tip, which is insertable into the body for both fluid delivery and for analyte monitoring. Upon insertion, the tip is rigidly connected to the well.
   b. A penetrating member, which is a sharpened piece used for skin pricking during tip insertion. It is removed upon insertion of the tip.
   c. A protector, which shields the cannula/probe and the penetrating member.

In some embodiments, the tip insertion can be done automatically by virtue of a spring loaded inserter.

4. A remote control unit for controlling the patch unit.

In some embodiments, a system for infusing a therapeutic fluid into a body of a patient is provided and includes a skin adherable device comprising a dispensing apparatus, a multi-purpose tip for delivering the therapeutic fluid to the body of the patient and for monitoring bodily analyte in the body of the patient, and a remote control unit, including a blood glucose monitoring apparatus. The system optionally comprises a cradle which receives the skin adherable device and which includes an adhesive on a skin-facing surface.

The monitoring apparatus may employ a conventional analyte sensing means, including without limitation, such as optical, electrochemical, acoustic, or photo-acoustic.

In some embodiments, the device includes an external glucose monitoring and insulin dispensing unit which contains means to dispense insulin according to glucose levels in a closed or semi-closed loop system.

In some embodiments, the device includes one unit for continuous insulin delivery and continuous glucose monitoring using one common insertion site and one tip.

In some embodiments, the device includes an external single glucose monitoring and insulin dispensing unit that can be comprised of one part or two parts and can be connected and disconnected from the body at user's discretion.

In some embodiments, a stand alone tip can be inserted into the body, having a proximal end that remains out of the body and that can be connected and reconnected both to an insulin dispenser and glucose monitor.

In some embodiments, the device includes an external glucose monitoring and insulin dispensing unit that can be disconnected and reconnected to a tip inserted in the body.

In some embodiments, the device includes an external glucose monitoring and insulin dispensing unit that is highly cost-effective for the patient.

It is an object of some of the embodiments to provide a device that includes a unit for frequent or continuous measurements of bodily analyte levels and a unit for frequent or continuous delivery of therapeutic fluid into the body.

It is another object of some of the embodiments to provide a device that includes a unit for frequent or continuous measurements of glucose levels and a unit for frequent or continuous delivery of insulin.

It is another object of some of the embodiments to provide a device that includes a unit for frequent or continuous measurements of glucose levels and a unit for frequent or continuous delivery of insulin according to the monitored glucose levels.

It is another object of some of the embodiments to provide a device that is configured as a skin adherable unit which includes a glucose monitoring apparatus and an insulin dispensing apparatus.

It is another object of some embodiments to provide a single patch unit, in which the monitoring and dispensing apparatuses can concomitantly use a common insertion site and one tip that serves as a probe for monitoring glucose levels and as a cannula for delivering insulin. The glucose level may be monitored within the ISF in the subcutaneous tissue, and the insulin may be delivered into the subcutaneous tissue.

It is another object of some embodiments to provide a patch unit that includes monitoring and dispensing apparatuses and has two-parts—a reusable part and a disposable part. The reusable part may include relatively expensive components, e.g., electronics, a driving mechanism, and the disposable part may include relatively inexpensive components, e.g., a reservoir.

It is another object of some of the embodiments to provide a device that is configured as a patch unit and contains both a continuous glucose monitoring apparatus and insulin dispensing apparatus. The patch unit can be controlled by a remote control unit or by buttons provided anywhere on the patch unit.

It is another object of some embodiments to provide a patch unit capable both of analyte monitoring and fluid dispensing and that is thin, miniature, can be hidden under the clothes, can be attached to the patient's body at any desired location, avoid long tubing, and does not interfere with normal daily activities.

It is another object of some embodiments to provide a patch unit which includes both monitoring and dispensing apparatuses, where the patch unit can be connected to a tip insertable within various bodily tissue, including, for example, subcutaneous tissue, blood vessels, peritoneal cavity, muscles, and adipose tissue.

BRIEF DESCRIPTION OF THE DRAWINGS

FIGS. 1a-c show a device which can include a single-part monitoring and dispensing patch unit and a remote control unit. FIG. 1b shows a single-part monitoring and dispensing patch unit. FIG. 1c shows a two-part monitoring and dispensing patch unit.

FIG. 4a shows the inserter with the loaded cradle unit before loading the cartridge unit. FIG. 4b shows the inserter adherable to the skin loaded with the cradle unit and cartridge unit. FIG. 4c shows the insertion of the tip through the cradle unit and skin into the subcutaneous tissue. FIG. 4d shows the retraction of the penetrating member into the cartridge.

FIG. 10a shows a single-part patch unit and FIG. 10b shows a two-part patch unit.

FIG. 11a shows a single-part patch unit and FIG. 11b shows a two-part patch unit.

FIG. 12b shows a transverse cross sectional view of the electrodes on the outer surface of the tip.

FIGS. 13a-c show an embodiment of a two-part patch unit employing an electrochemical monitoring apparatus, where the patch unit is connected to the tip that has ring-like electrodes on its outer surface. FIG. 13b shows a longitudinal cross-sectional view of the electrodes on the outer surface of the tip. FIG. 13c shows a spatial view of the electrodes.

FIG. 26a shows a peristaltic mechanism and FIG. 26b shows a plunger/piston mechanism.

FIG. 27a shows wiring and connectors within the patch unit. FIG. 27b shows wiring and connectors within the cradle unit.

DETAILED DESCRIPTION

FIG. 1a shows the device which includes a patch unit (10). The patch unit contains a dispensing apparatus and a monitoring apparatus. The device also includes a remote control unit (40) for controlling the patch unit (10). In some embodiments, the patch unit (10) can be configured to include a single part (shown in FIG. 1b) or two parts (shown in FIG. 1c). In some embodiments, the patch unit (10) can be configured to include a reusable part (100) and a disposable part (200).

Figure 2A:
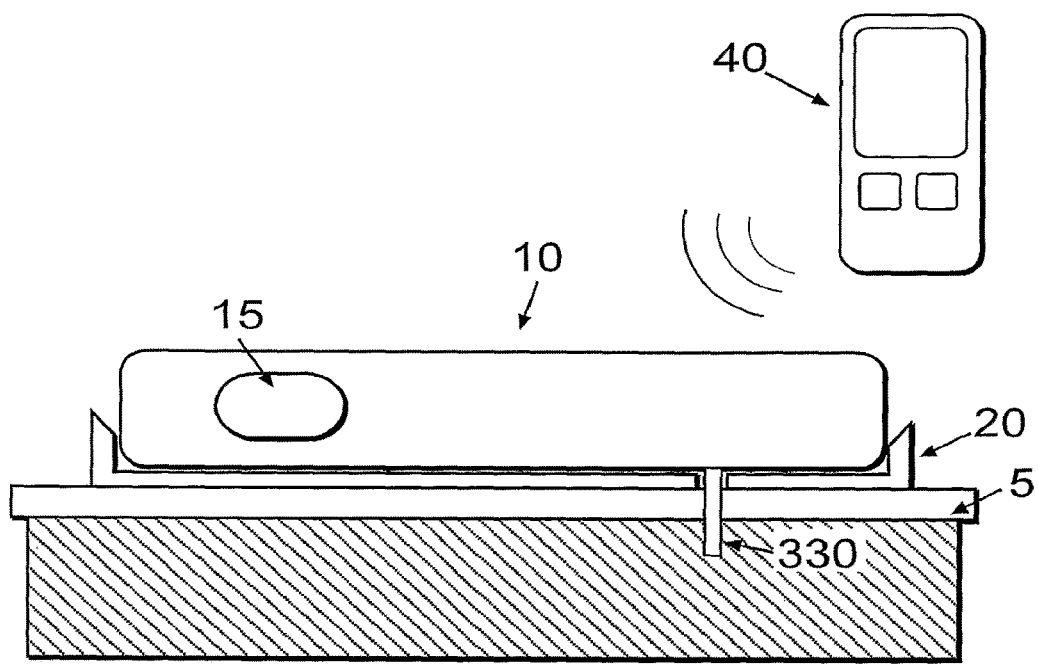
FIG. 2a shows an embodiment of a single-part monitoring and dispensing patch unit.

FIG. 2a shows a single-part patch unit (10), as well as a skin adherable cradle unit (20) and a remote control unit (40). The patch unit (10) may be connected to or disconnected from the cradle unit (20) upon user discretion. Upon connection of the patch unit (10) to cradle unit (20) fluid communication is established between the reservoir provided in the patch unit (10) (not shown in FIG. 2a) and a subcutaneously insertable tip (330). As can be understood by one skilled in the art, even though it is not specifically shown in FIG. 2a, a suitable electrical wiring connection can be provided between the tip (330) and the patch unit (10). Fluid delivery from the patch unit can be programmed by the remote control unit (40) or manually by at least one button (15) provided on the patch unit (10). The remote control unit (40) may also be used for user inputs, monitoring, programming and user feedback.

Figure 2B:
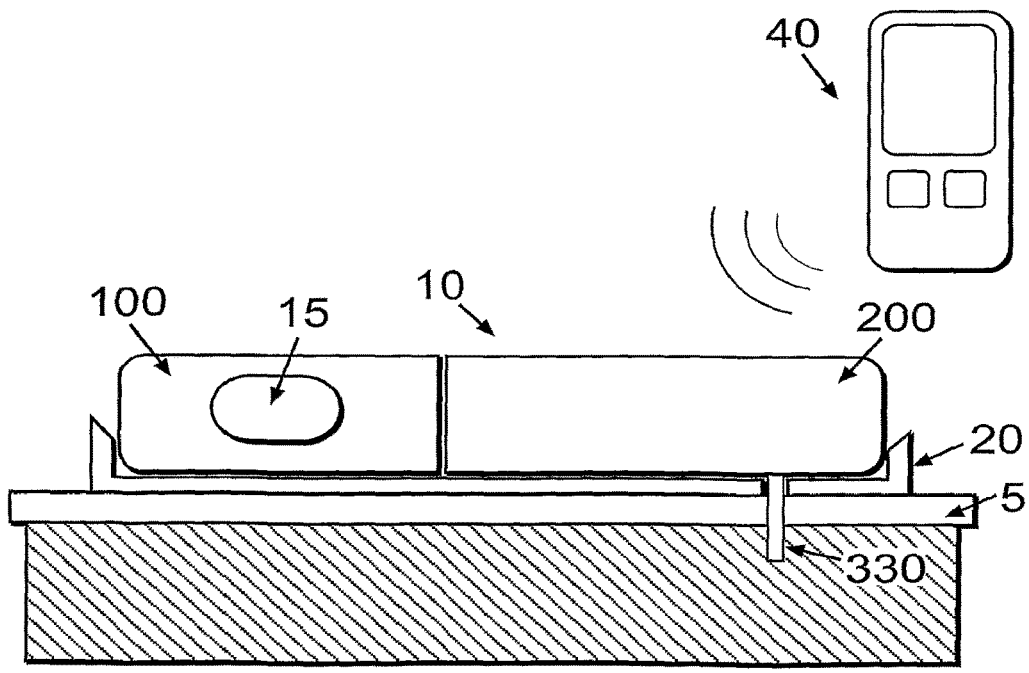
FIG. 2b shows an embodiment of a two-part monitoring and dispensing patch unit with a remote control unit and a cradle unit.

FIG. 2b shows a device which is configured as a two-part patch unit (10) having a reusable part (100) and a disposable part (200). The device further includes the cradle unit (20) and the remote control unit (40). The reusable part (100) is contained within one housing and the disposable part (200) is contained within another separate housing. The reusable and disposable parts housings are connected to each other before operation of the patch unit (10). Connection of the patch unit (10) to the cradle unit (20) provides fluid communication between the reservoir (not shown in FIG. 2b) located in the disposable part (200) and the tip (330). An electrical wiring connection is also established (not shown in FIG. 2b) between the tip (330) and the disposable part (200) of the patch unit (10). Fluid delivery can be programmed by the remote control unit (40) and/or manually by at least one button (15) provided on the reusable part housing. The remote control unit (40) may also be used for user inputs, monitoring, programming, and user feedback. In some embodiments, data acquisition and monitoring can be performed by a processing unit located in the reusable part's housing. The results of such monitoring can be shown on a screen located on the reusable part's housing.

Figure 3A:
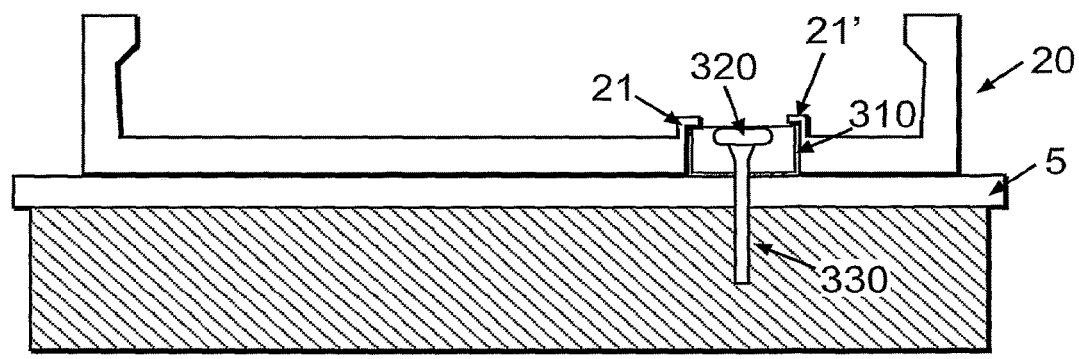
FIGS. 3a-b show respectively a cross-sectional view and a top view of an embodiment of the cradle unit.
Figure 3B:
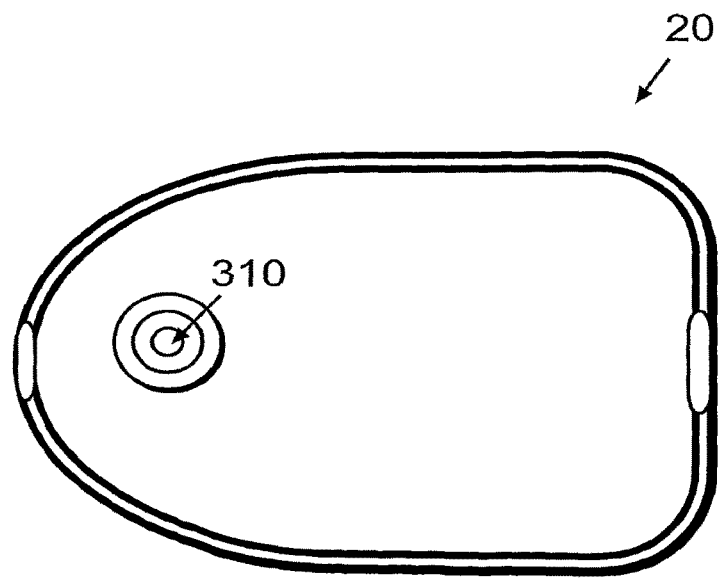

FIGS. 3a-b show a cross-sectional view (FIG. 3a) and a top view (FIG. 3b) of the cradle unit (20) and the subcutaneously insertable tip (330). The downwardly facing surface of the cradle unit (20) is covered by a flat sheet with an adhesive layer facing the skin (5). The cradle unit (20) is also provided with a connector for connecting and disconnecting the patch unit (10). An example of a suitable connector could be two latches. The cradle unit (20) further includes a well (310), which is an opening used as a passageway for the tip (330). The well (310) includes protrusions extending upwardly (21, 21') for anchoring the tip (330) to the cradle unit (20) after tip insertion. The tip (330) is provided with an opening at its distal end and with a self sealable rubber septum (320) at its proximal end. The septum (320) can be pierced by a connecting lumen provided in the patch unit (10) (not shown in FIGS. 3a-b). The tip (330) can be inserted automatically using an inserter or manually.

Figure 4A:
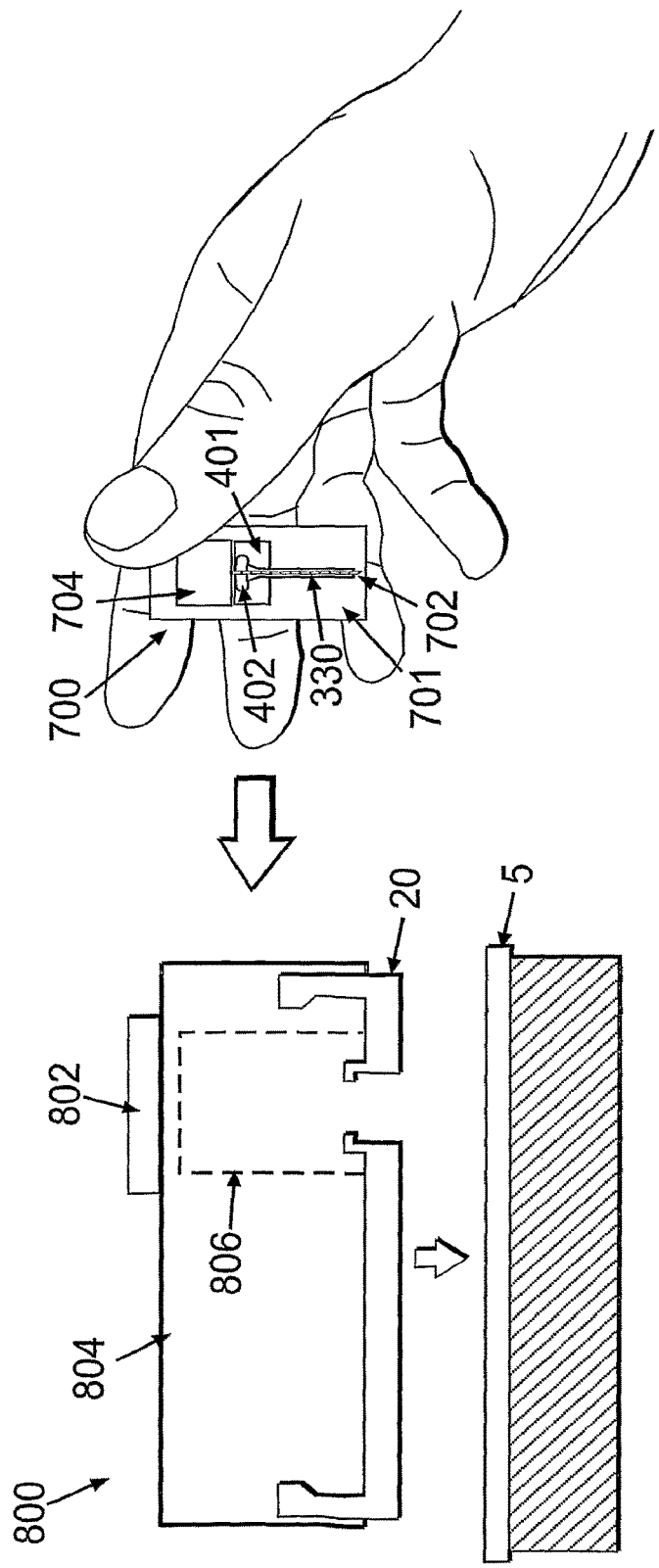
FIGS. 4a-d illustrate tip insertion, according to some embodiments of the provided systems, devices and methods.

In the following discussion, the term "cannula" will also be used to refer to the tip (330). Detailed discussion of cannula insertion is provided in the co-owned/co-pending U.S. Provisional Patent Application No. 60/876,679, the disclosure of which is incorporated herein by reference in its entirety. FIGS. 4a-d show an embodiment of the cannula insertion and cradle unit (20) adherence. Insertion of the tip (330) can be carried out manually (not shown in FIGS. 4a-d), or automatically with an insertion device (800), which is preloaded with a dedicated cannula cartridge unit (700). FIG. 4a shows the insertion device ("inserter") (800) before it is loaded with the cannula cartridge unit (700) depicted on the right side of the FIG. 4a. The cannula cartridge unit (700) includes a soft cannula (330) surrounded by penetrating member (702). The cannula has a grip portion (704), rubber septum (402), and cannula hub (401) for anchoring. The cannula cartridge unit (700) is enclosed within a protector (701) that maintains sterility, avoids unintentional pricking, and facilitates inserter loading. The cannula cartridge unit (700) is discussed in the co-owned/co-pending U.S. Provisional Patent Application No. 60/937,155, and the insertion method is discussed in the co-owned/co-pending U.S. Provisional Patent Application No. 60/937,214, the disclosures of which are each incorporated herein by reference in their entireties.

The insertion device (800) includes a housing (804) in which the cradle (20) can be loaded. The housing has also a slot (806) into which the cannula cartridge unit (700) can be loaded, and a button (802) which initiates the insertion operation.

Figure 4B:
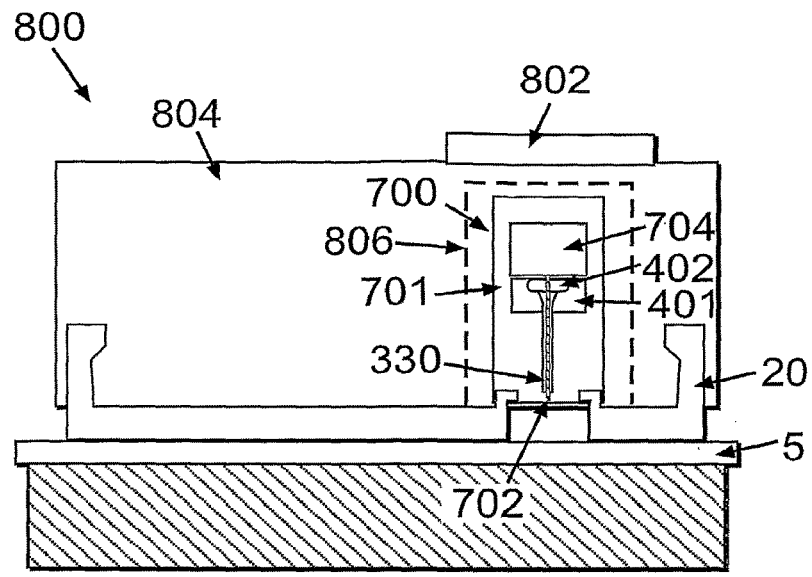
Figure 4C:
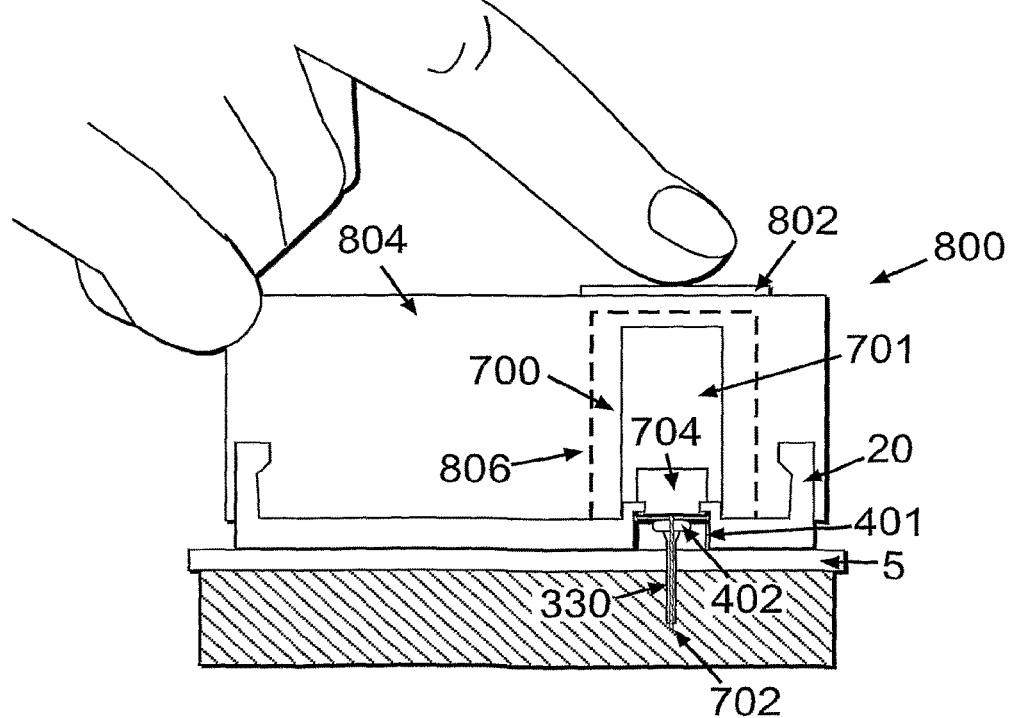
Figure 4D:
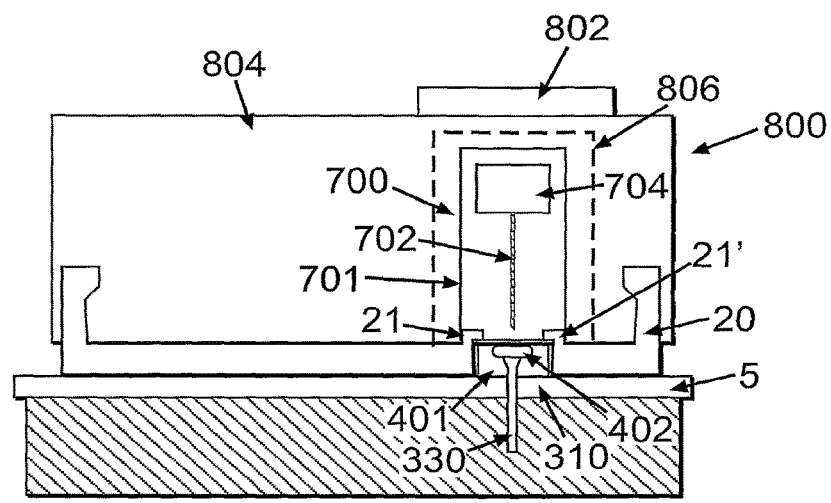

FIG. 4b shows the insertion device (800) after it has been loaded with the cannula cartridge unit (700) and with the cradle unit (20) already adhered to the skin but the cannula (330) not yet inserted. FIG. 4c shows schematically the insertion of the cannula (330) into the patient's skin (5) by pressing the button (802). FIG. 4d shows the retraction of the penetrating member (702) by gripping the grip portion (704). The cannula (330) is left positioned within the subcutaneous compartment. The cannula hub (401) is secured in the well by the anchors (21 and 21').

Figure 5:
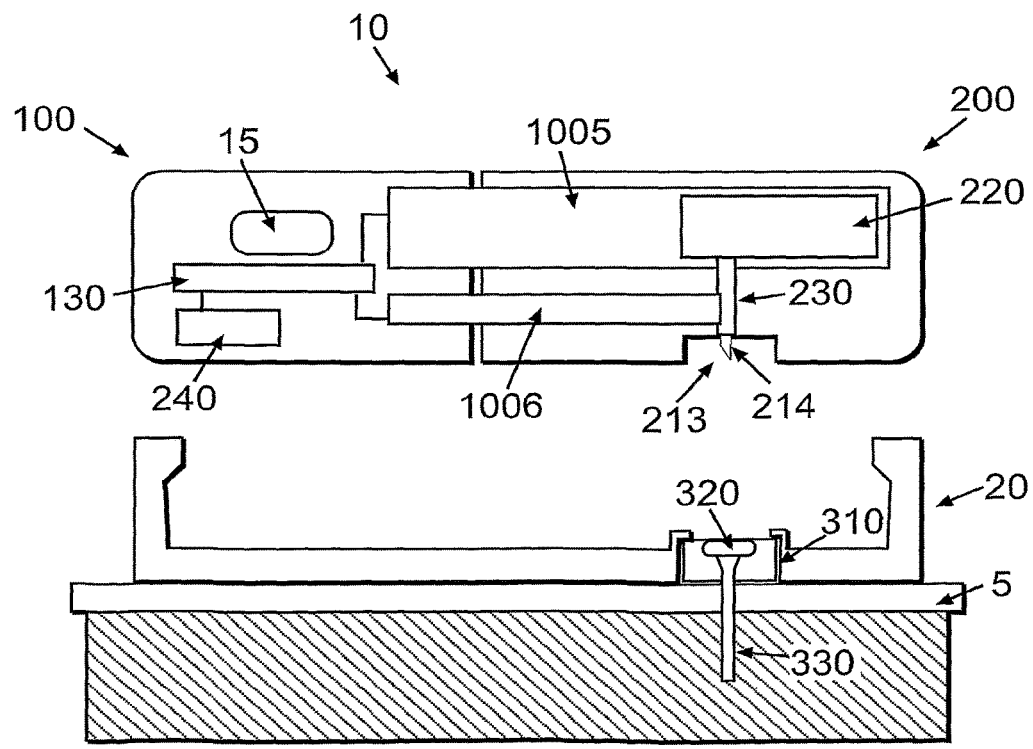
FIG. 5 shows a cross-sectional view of an embodiment of the two-part patch unit and the cradle unit before connection.

FIG. 5 shows a cross-sectional view of the two-part patch unit (10) having a reusable part (100) and a disposable part (200). The patch unit (10) contains a dispensing apparatus (1005) and a monitoring apparatus (1006), each including at least one component residing within the disposable or the reusable parts. The reusable part (100) further includes electronics (130), which contains a processor-controller (not shown) and may include an energy supply (240). The disposable part (200) contains a reservoir (220), delivery tube (230), and outlet port (213), to which is connected the delivery tube (230). In some embodiments, the energy supply (240) can be provided in the disposable part (200). At the outlet port (213), there is provided a connecting lumen (214) which is adapted to pierce the rubber septum (320) of the cannula (330) after connection of the patch unit (10) to the cradle unit (20). The distal end of the cannula (330) is seen being located within the subcutaneous tissue below the skin (5). The proximal end of the cannula is secured at the well (310). Manual operation buttons (15) may be provided on the housing of the reusable part (100).

Figure 6A:
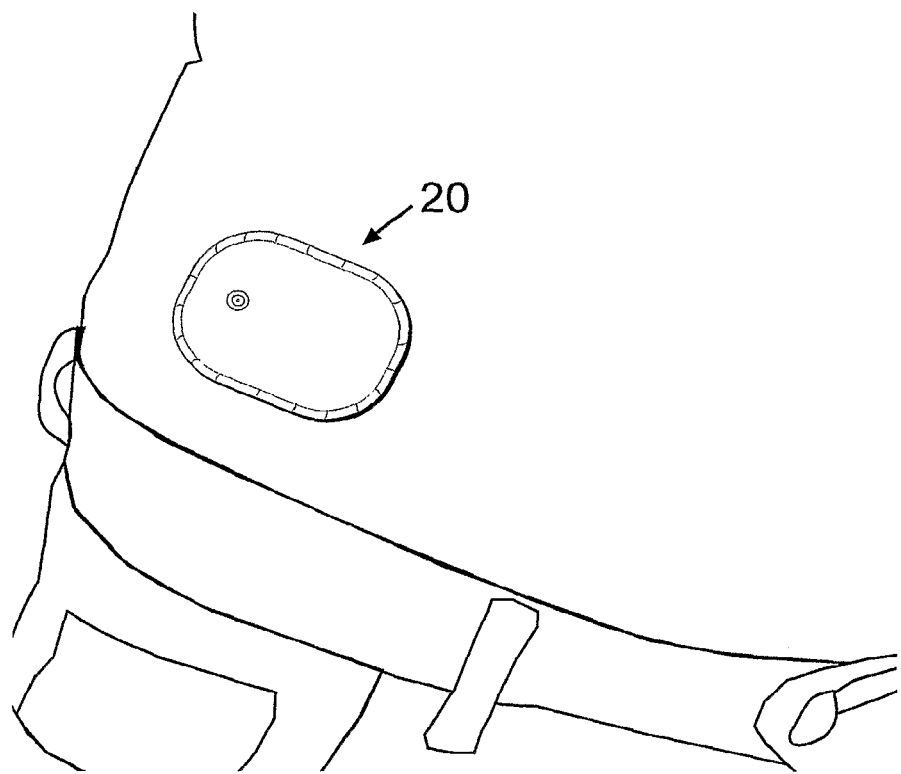
FIGS. 6a-c show a connection of the patch unit to the cradle unit.
Figure 6B:
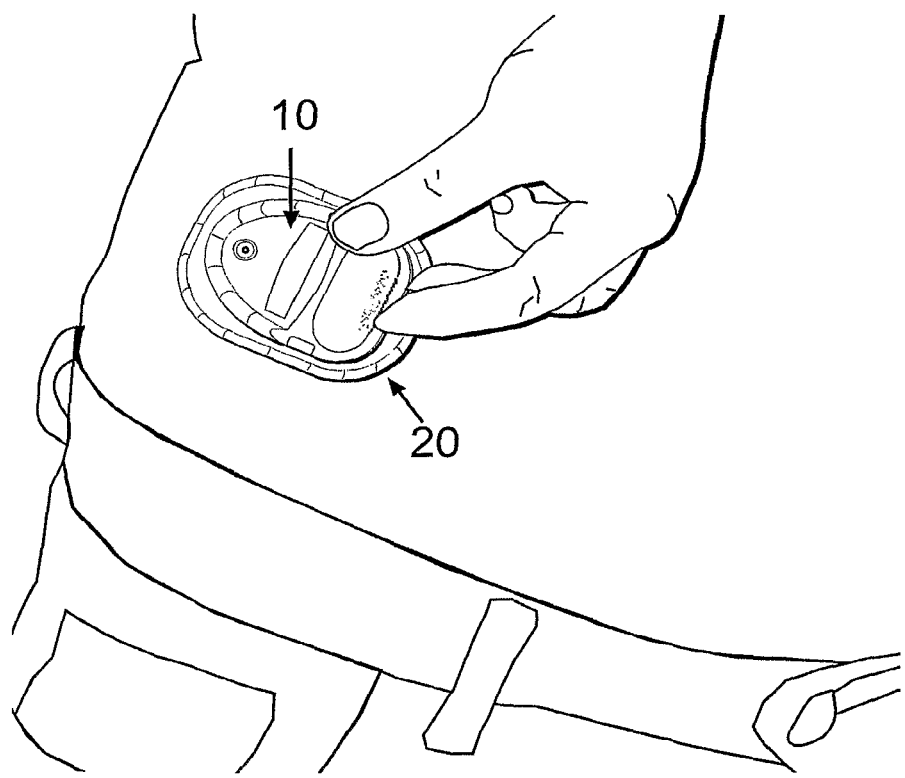
Figure 6C:
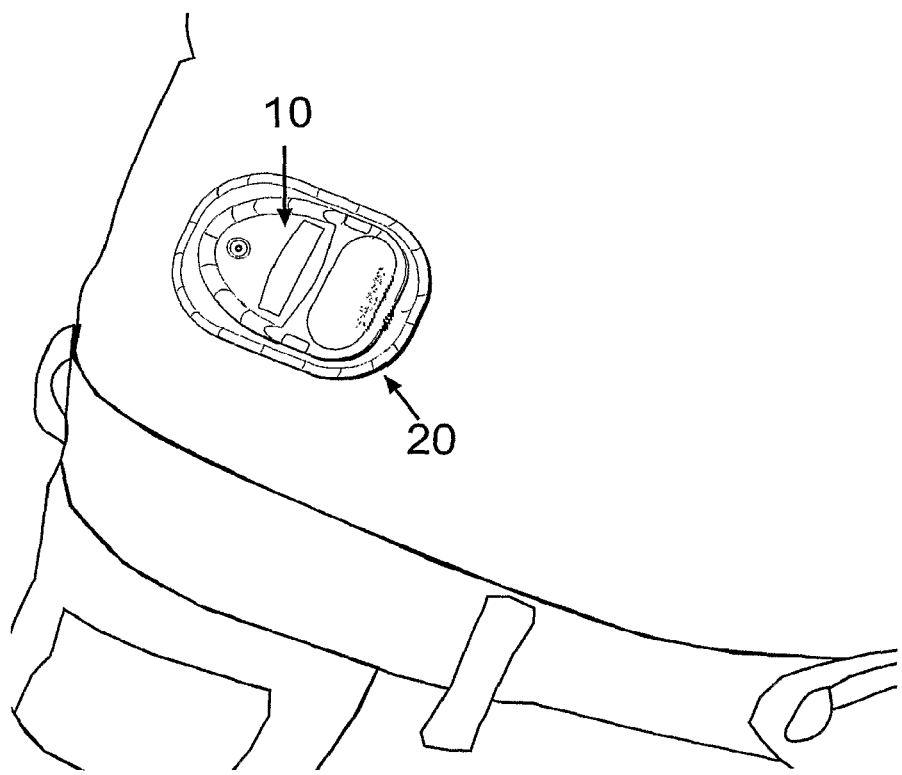

FIGS. 6a-c show the connection of the patch unit (10) to the body via the cradle unit (20). FIG. 6a shows the cradle unit (20) being adhered to the skin of a user. FIG. 6b shows the connection of the patch unit (10) to the cradle unit (20). FIG. 6c shows the patch unit (10) after it has been connected to cradle unit (20).

Figure 7A:
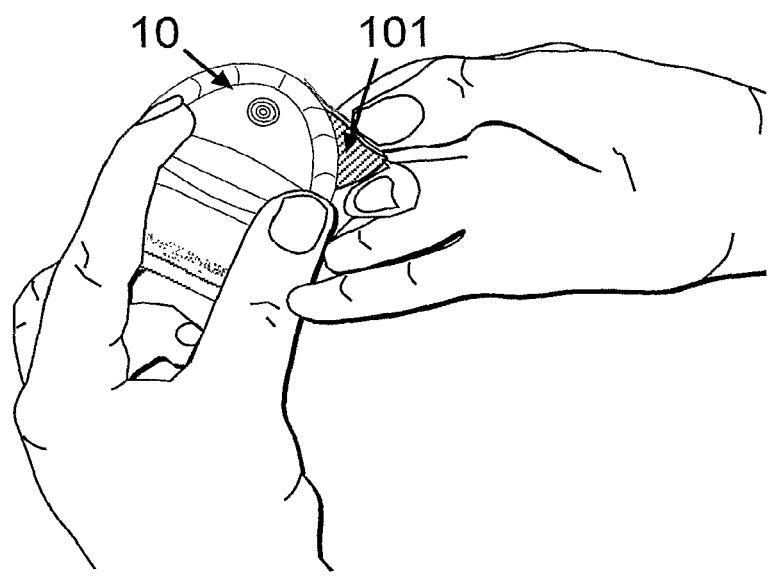
FIGS. 7a-c show a direct adhesion of the patch unit to skin.
Figure 7B:
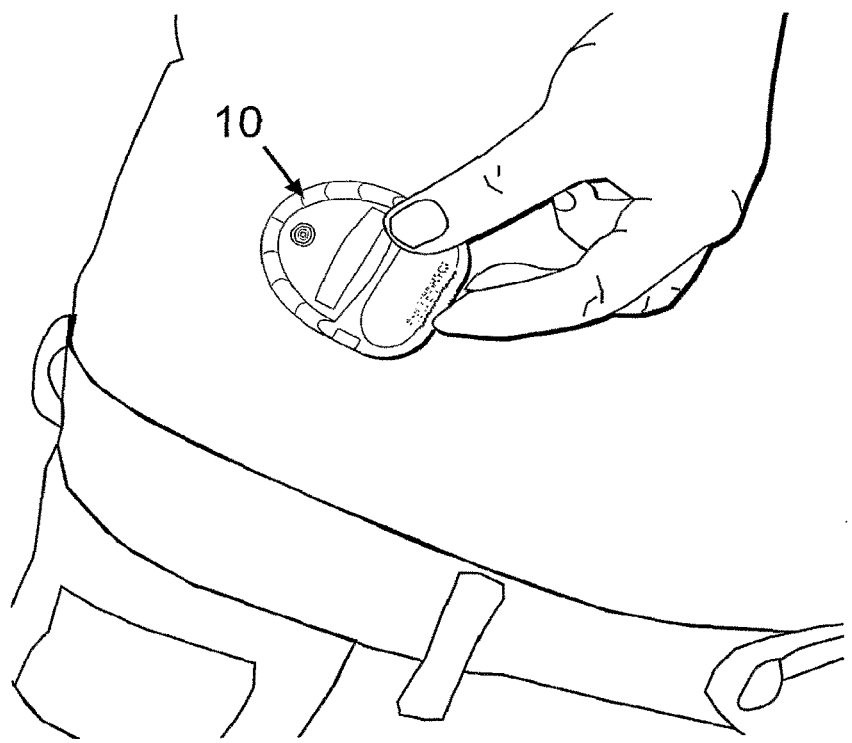
Figure 7C:
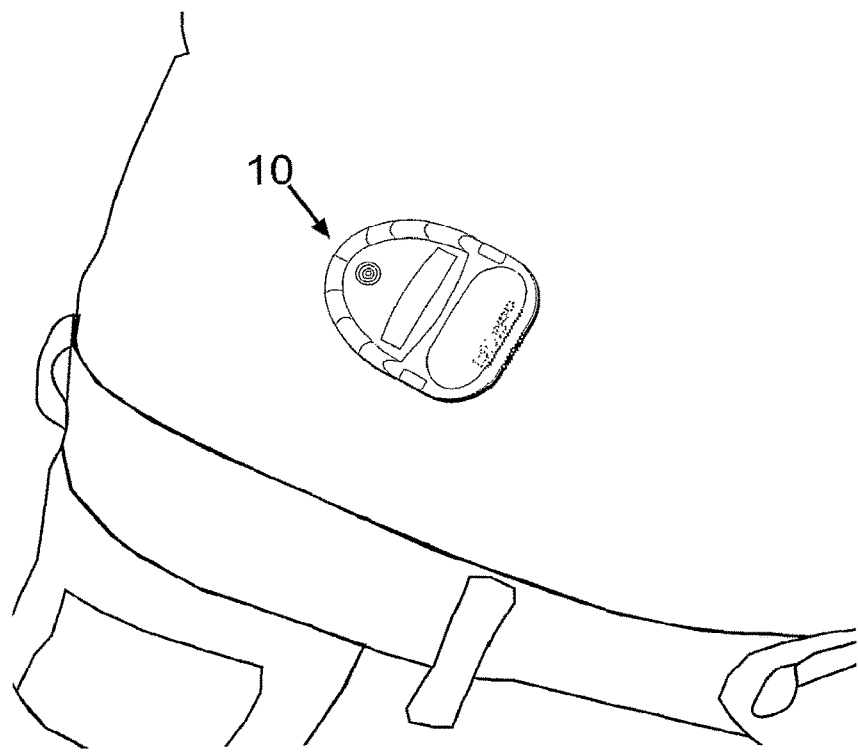

FIGS. 7a-c show adhesion of the patch unit (10) directly to the body and not via the cradle unit (20). In this embodiment, the adhesive is attached to the disposable part (200) and there is no cradle unit (20). FIG. 7a shows the peeling of the adhesive (101) from the bottom surface of the patch unit (10). FIG. 7b shows adhesive connection of the patch unit (10) to the skin. FIG. 7c shows the patch unit (10) after it has been connected to the user's body.

Figure 8:
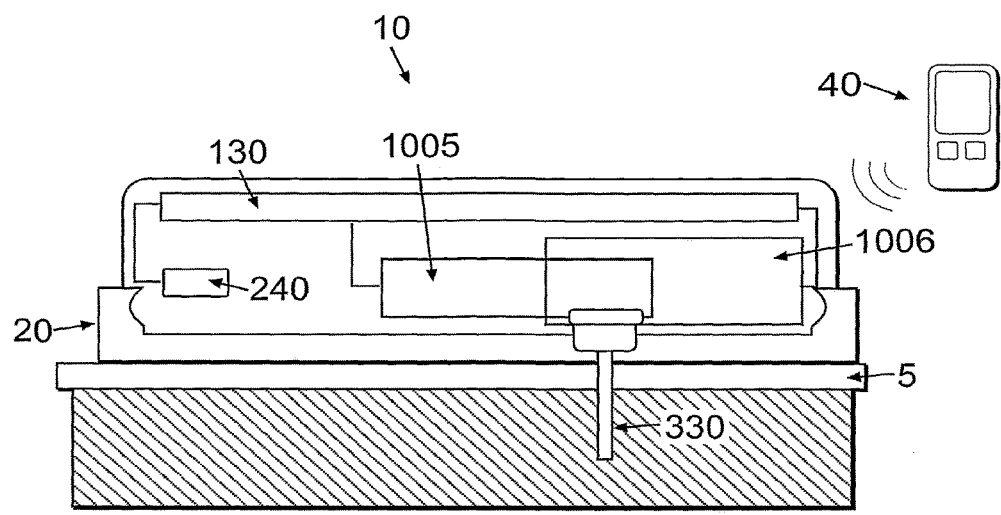
FIG. 8 shows an embodiment of the device that includes the patch unit and a remote control unit, where the patch unit is connected to a single tip.

FIG. 8 shows a patch unit (10) that is provided with a single tip (330). In this configuration, the same cannula which is used for fluid delivery serves also as a probe for the analyte monitoring. The patch unit (10) includes the dispensing apparatus (1005), the monitoring apparatus (1006), electronics (130), and an energy supply (240). All these components are disposed within a single unit which can be attached to the user's skin (5) either directly or via the cradle unit (20). A single tip (330), which can be configured with any cross-sectional shape, including without limitation, circular, oval, rectangular, or triangular, is inserted into the subcutaneous tissue to provide for fluid delivery to the user's body (thus, serving as a cannula) and monitoring of analytes within the user's body (thus serving as a probe). The remote control unit (40) may be used for remote or direct programming and/or data handling.

In some embodiments, the dispensed fluid is insulin, the monitored analyte is glucose and the subcutaneous compartment includes ISF. Insulin may be continuously (or in short intervals, such as every 3-10 minutes) dispensed into the subcutaneous compartment by the dispensing apparatus (1005) through the tip (330). Glucose levels can be measured continuously, or periodically in short intervals, by the monitoring apparatus (1006), using the tip (330).

Figure 9:
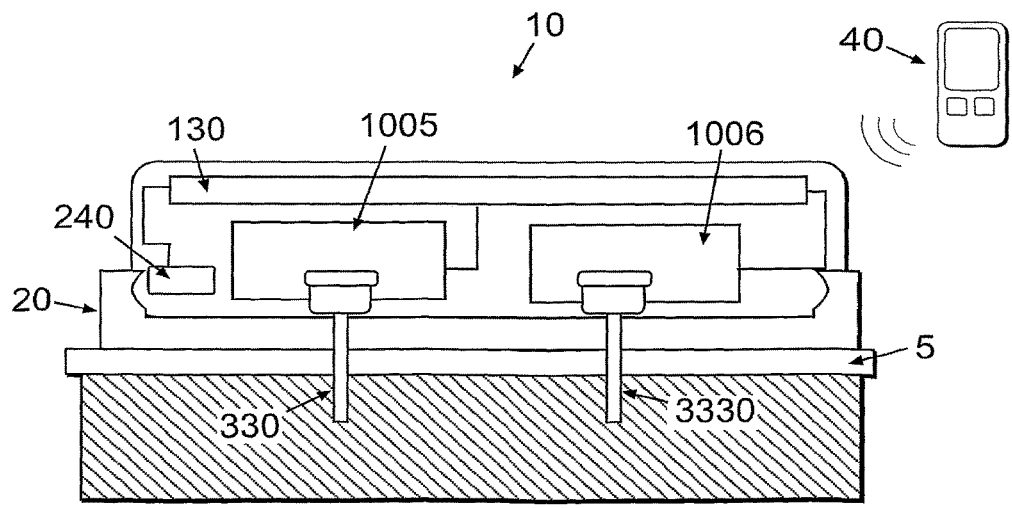
FIG. 9 shows an embodiment of the device including the remote control unit and the patch unit, where the patch unit is connected to two tips.

FIG. 9 shows another embodiment of the patch unit (10) which can be connected to the body via cradle unit (20). In the shown embodiment, the cradle unit (20) is provided with two passageways, one for cannula (330) and the second for a probe (3330). The patch unit includes a dispensing apparatus (1005), a monitoring apparatus (1006), electronics (130), and an energy supply (240). In some embodiments, the dispensing apparatus (1005) includes one or more components of an insulin pump (e.g., a reservoir, driving mechanism, and pumping mechanism). The dispensing apparatus (1005) also has an outlet port that can be connected to the cannula (330). In some embodiments, the monitoring apparatus (1006) can include one or more components of a continuous glucose monitor, and it can be connected to a probe (3330). The remote control unit (40) may be used for remote programming and/or data handling of both the dispensing apparatus (1005) and monitoring apparatus (1006).

The single patch unit (10) containing the dispensing apparatus (1005) and monitoring apparatus (1006) can be a single-part or a two-part (reusable and disposable) patch unit (10). The patch unit (10) can be contained in one or two housings. Further, the patch unit (10) can be operated by a remote control unit (40) and/or by manual buttons (not shown in FIG. 9) located on the patch housing. In some embodiments, each one of the cannula (330) and probe (3330) can be similar to the tip (330) shown in FIG. 8.

Figure 10A:
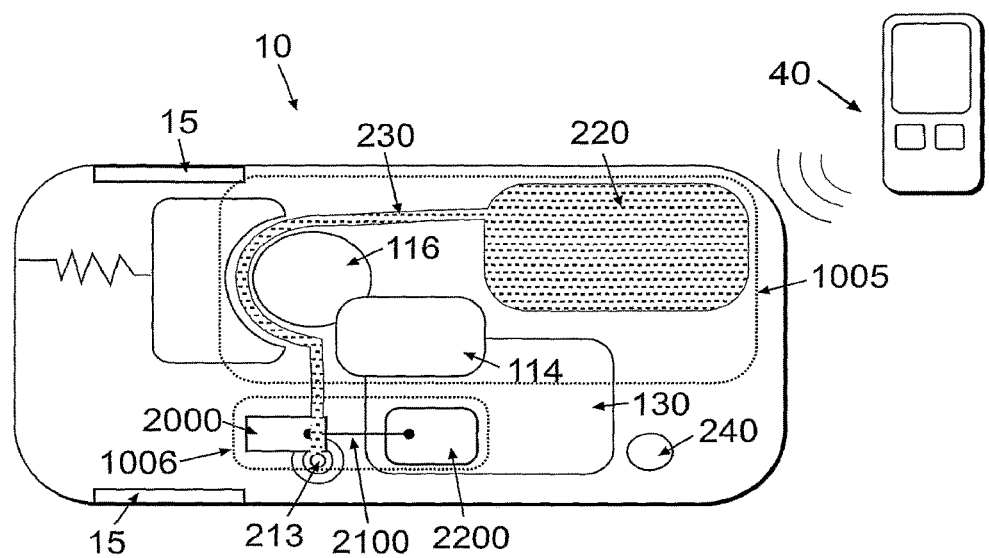
FIGS. 10a-b show an embodiment of the device that includes a patch unit and a remote control unit, where the dispensing apparatus employs a peristaltic pumping mechanism.

FIG. 10a shows an embodiment of a one-part patch unit (10) that includes a monitoring apparatus (1006) and dispensing apparatus (1005) which employs a peristaltic pumping mechanism (116). Fluid is delivered from reservoir (220) through delivery tube (230) to the outlet port (213) by means of a peristaltic pumping mechanism (116). There is provided a sensing means (2000) situated near the outlet port (213) and having access to the interior of the delivery tube (230). The sensing means (2000) is electrically connected by wires (2100) to a processor-controller (2200). Subcutaneous analyte concentration levels are measured by the sensing means (2000) and signals are transported through wires (2100) to be analyzed by the processor-controller (2200). The pumping mechanism (116) can be activated by a driving mechanism (114). In some embodiments, the driving mechanism (114), which actuates the pumping mechanism (116), can include without limitation a stepper motor, DC motor, or SMA actuator. An energy supply (240) can also be provided, which can be one or more batteries. The dispensing apparatus (1005) and the monitoring apparatus (1006) are configured to be controlled by a PCB having electronics (130), which may also contain the processor-controller (2200). Programming can be done by the remote control unit (40) and/or by at least one button (15) provided on the patch unit (10).

Figure 10B:
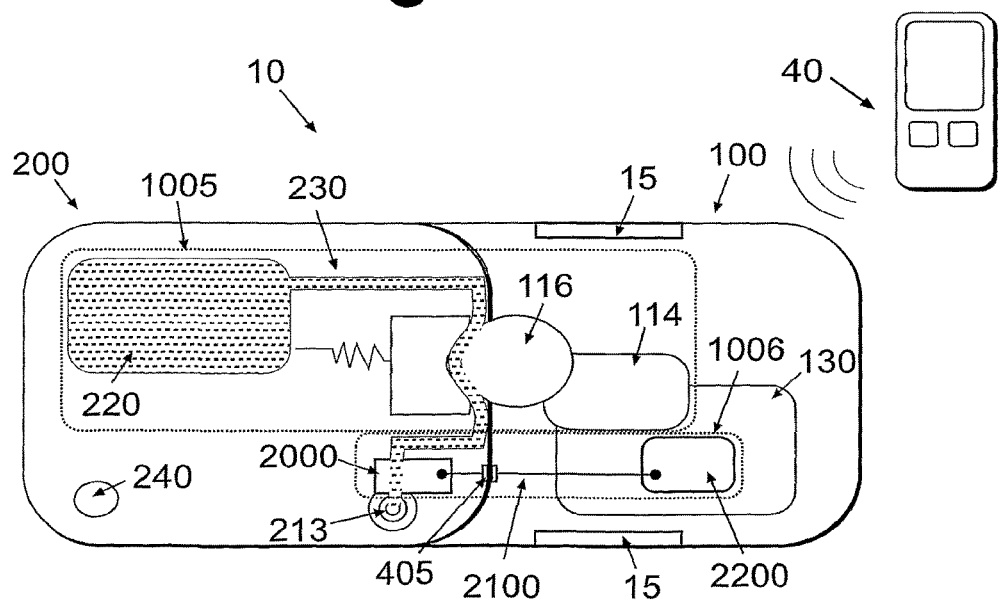

FIG. 10b shows an embodiment of a two-part patch unit (10) that includes a monitoring apparatus (1006) and a dispensing apparatus (1005) which employs a peristaltic pumping mechanism (116). The two-part patch unit (10) includes a reusable part (100) and a disposable part (200), wherein each part can be contained in a separate housing. The reusable part (100) includes the relatively expensive components of the monitoring and dispensing apparatuses, including without limitation, a driving mechanism (114), a pumping mechanism (116), electronics (130), and a processor-controller (2200). At least one manual operating button (15) can be provided for operating the patch unit (10) and can be located on the reusable part (100). The disposable part (200) includes an outlet port (213) and relatively cheap components of the dispensing apparatus, including without limitation, a reservoir (220), a delivery tube (230), energy supply (240), and relatively cheap components of the monitoring apparatus (1006), including without limitation, wires (2100) and connectors (405). The monitoring apparatus' sensing means (2000) can be located within the disposable part (200) (extrinsic configuration) or on the tip (intrinsic configuration), as discussed below in connection with FIGS. 20a and 20b, respectively. In some embodiments, the energy supply (240) can be contained in the reusable part (100). Analyte monitoring and fluid dispensing can be done after connecting and pairing the reusable part (100) to the disposable part (200) and after connecting the two paired parts to the cradle unit (20) (not shown) and to the tip (330). A detailed discussion of the fluid dispensing can be found in the co-owned/co-pending U.S. patent application Ser. No. 11/397,115 and International Patent Application No. PCT/IL06/001276, the disclosures of which are incorporated herein by reference in their entireties. A detailed discussion of analyte monitoring can be found in the co-owned/co-pending U.S. patent application Ser. No. 11/706,606, U.S. Provisional Patent Application No. 60/876,945 and International Patent Applications Nos. PCT/IL07/001096 and PCT/IL07/001177, the disclosures of which are each incorporated herein by reference in their entireties.

In some embodiments, programming can be done by the remote control unit (40) and/or by at least one button (15) provided at the patch unit (10). As can be understood by one skilled in the art, the dispensing apparatus can include various types of pumping mechanisms (e.g., peristaltic pump or plunger movement within a syringe) and various driving mechanisms (e.g., DC or stepper motors, SMA derived motors, piezo, or bellow). As can also be understood by one skilled in the art, the monitoring apparatus (1006) can include various types of monitoring mechanisms (e.g., electrochemical, optical, acoustic, or any combination of known methods for analyte monitoring).

Figure 11A:
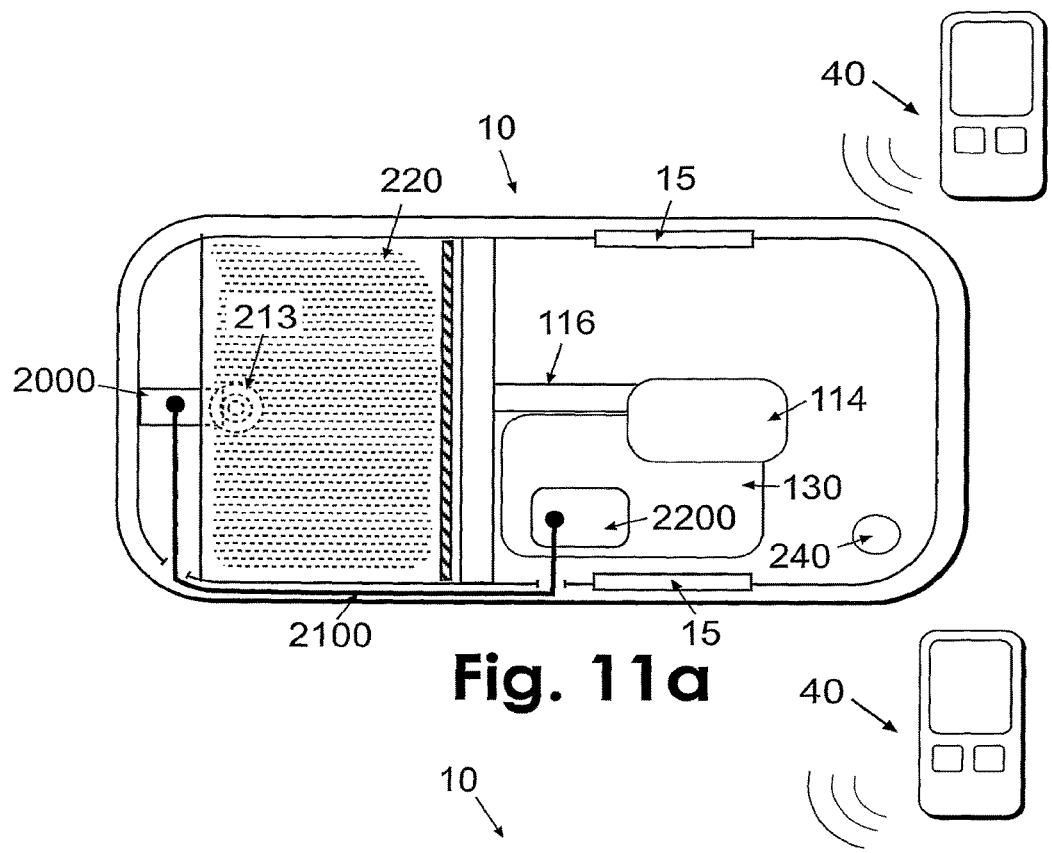
FIGS. 11a-b show an embodiment of the device that includes a patch unit and a remote control unit, where the dispensing apparatus employs a plunger/piston pumping mechanism.

FIG. 11a illustrates an embodiment of the one-part patch unit (10) that includes a monitoring apparatus and dispensing apparatus, which employs a plunger/piston pumping mechanism. Fluid is delivered from reservoir (220) to the outlet port (213) by means of a plunger/piston pumping mechanism (116). Sensing means (2000) is electrically connected by wires (2100) to processor-controller (2200). Subcutaneous analyte concentration levels are measured by the sensing means (2000) and signals are transported through wires (2100) to be analyzed by the processor-controller (2200). The pumping mechanism (116) can be actuated by driving mechanism (114). In some embodiments, the driving mechanism (114), which actuates the pumping mechanism (116), can include without limitation, a stepper motor, DC motor, or SMA actuator. An energy supply (240) can also be provided, which can be one or more batteries. The dispensing apparatus and the monitoring apparatus are configured to be controlled by a PCB having electronics (130), which may contain processor-controller (2200). Programming can be done by the remote control unit (40) and/or by at least one button (15) provided at the patch unit (10).

Figure 11B:
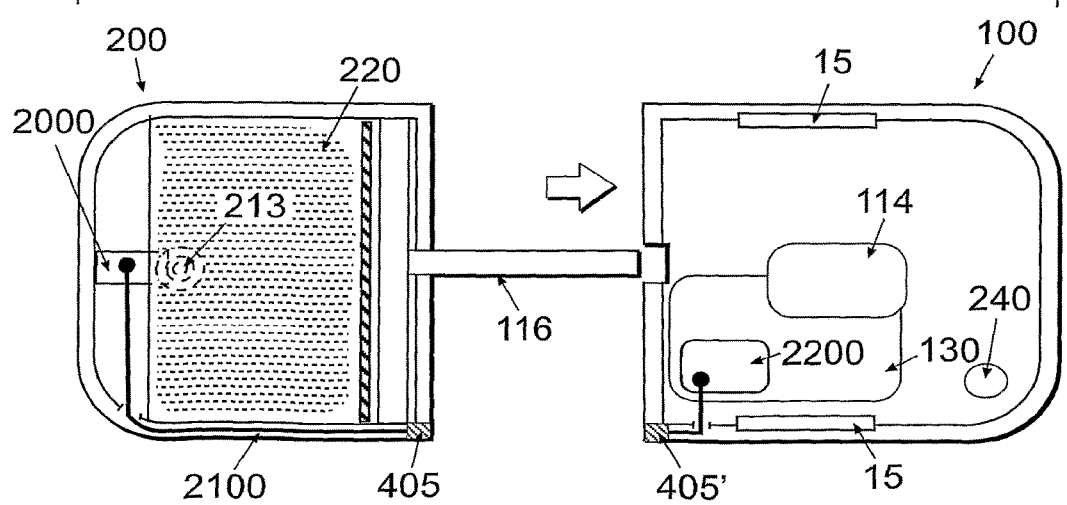

FIG. 11b illustrates an exemplary embodiment of a two-part patch unit (10) that includes a monitoring apparatus and dispensing apparatus, which employs a plunger/piston pumping mechanism (116). The two-part patch unit (10) includes a reusable part (100) and a disposable part (200), where each part can be contained in a separate housing. The reusable part (100) includes the relatively expensive components of the monitoring and dispensing apparatuses, which may include without limitation, a driving mechanism (114), pumping mechanism (116), electronics (130), and processor-controller (2200). At least one manual operating button (15) can be provided on the reusable part (100). The disposable part (200) includes outlet port (213), relatively cheap components of the dispensing apparatus, which may include without limitation, a reservoir (220), energy supply (240), and relatively cheap components of the monitoring apparatus, which may include wires (2100) and electrical connectors (405, 405'). The monitoring apparatus sensing means (2000) can be located within the disposable part (200) (extrinsic configuration) or on the tip (intrinsic configuration) as will be detailed further, for example, in FIGS. 20a and 20b, respectively. In some embodiments, the energy supply (240) can be contained in the reusable part (100). Analyte monitoring and fluid dispensing can be done after connecting and pairing the reusable part (100) to the disposable part (200), connecting connectors (405,405'), and connecting the two paired parts to the cradle unit (20) (not shown) and tip (330).

Figure 14:
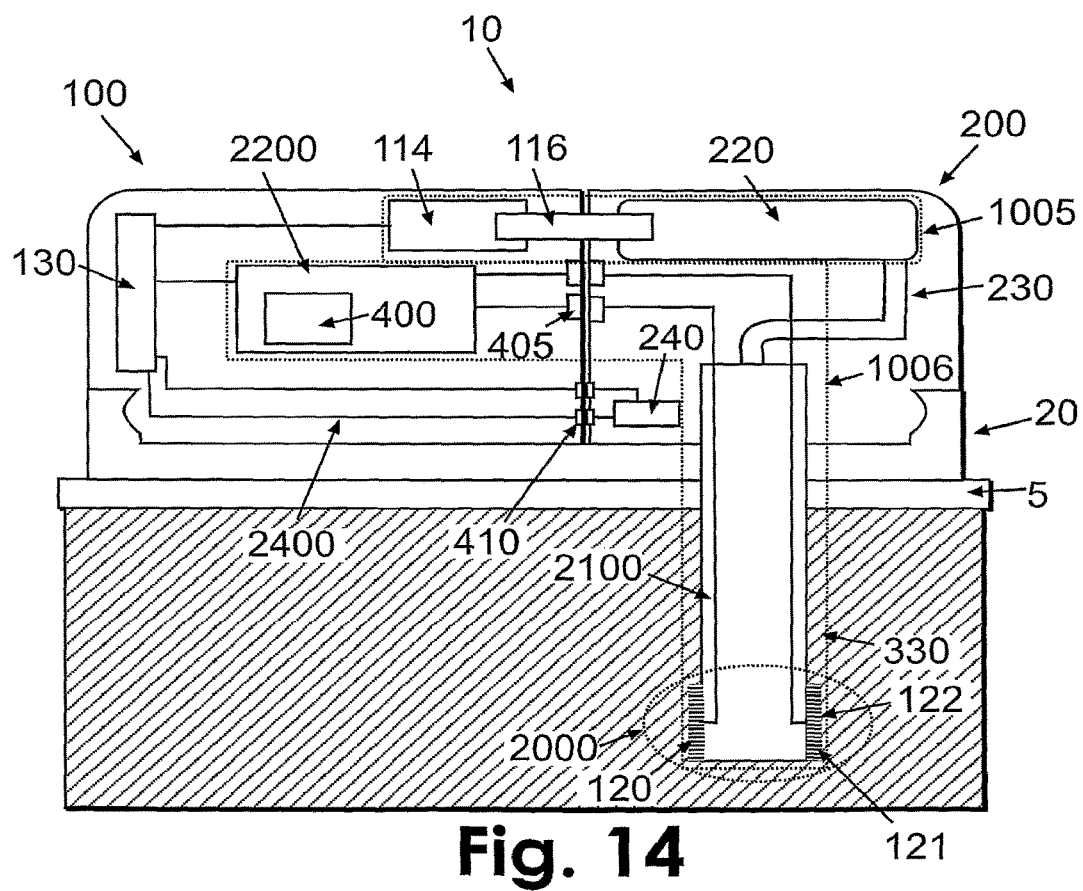
FIG. 14 illustrates in detail an embodiment of a two-part patch unit connected to the tip and employing an electrochemical monitoring apparatus.

FIGS. 12-14 illustrate an embodiment of the two-part patch unit (10), which includes a dispensing apparatus (1005) employing a piston-plunger pumping mechanism (116) and a monitoring apparatus (1006) employing an electrochemical sensing mechanism. The dispensing apparatus (1005) includes driving mechanism (114) and pumping mechanism (116), which are contained in the reusable part (100), and reservoir (220), delivery tube (230), energy supply (240) and the outlet port (not shown), which are contained in the disposable part (200). The electronic components (130) are located in the reusable part (100) and can be used both by the dispensing and monitoring apparatuses. Power is supplied to the reusable part (100) from the energy supply (240) located in the disposable part (200), by wires (2400) and connectors (410) that close the electrical circuit after pairing with the disposable part (200). In some embodiments, the energy supply (240) can be located in the reusable part (100). The patch unit (10) is connectable to tip (330), which can be inserted in the subcutaneous tissue.

Figure 12A:
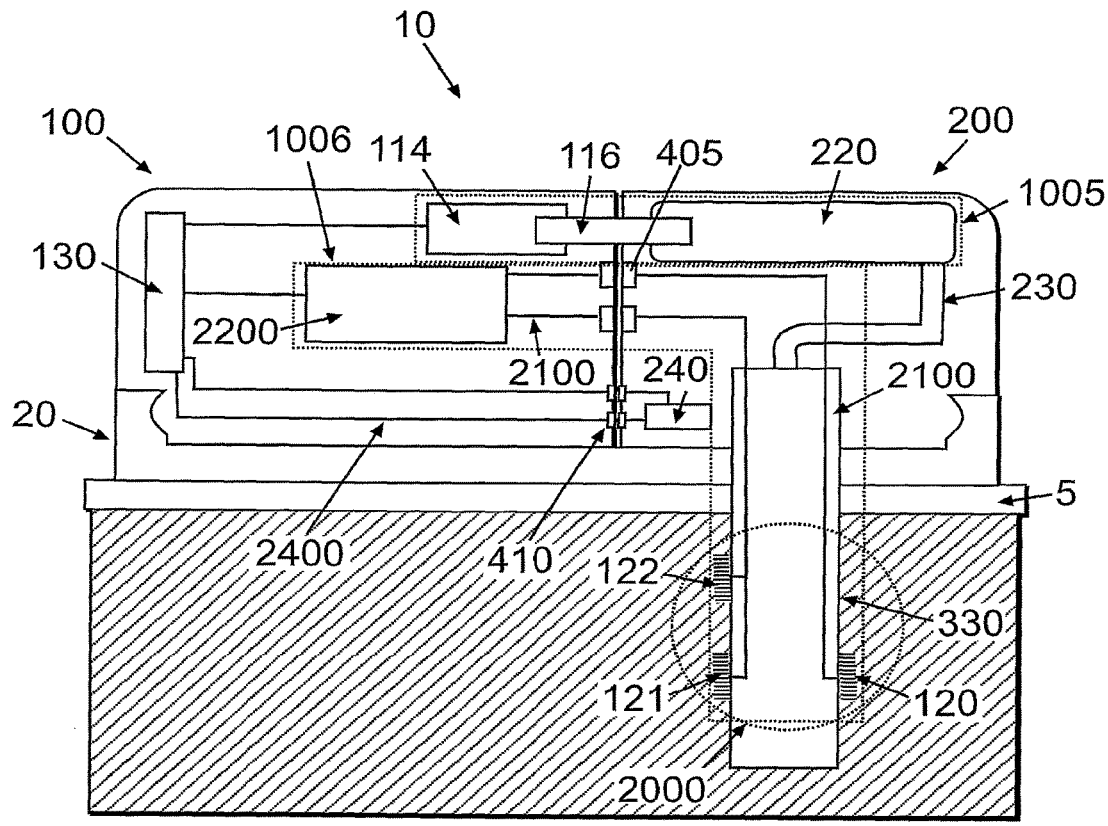
FIGS. 12a-b show an embodiment of a two-part patch unit employing an electrochemical monitoring apparatus, where the patch unit is connected to the tip that has electrodes on its outer surface.
Figure 12B:
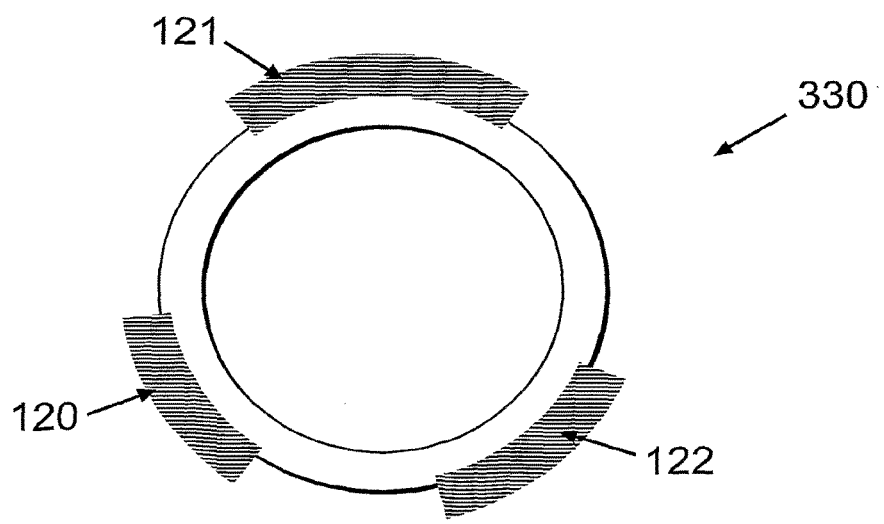

As illustrated in FIGS. 12a and 12b, the single tip (330) has electrodes (120, 121, 122) longitudinally deployed on its outer surface. One of the electrodes is a working electrode, the other is a counter electrode and the third electrode is a reference electrode. The monitoring apparatus (1006) includes sensing means (2000) having electrodes (120, 121, 122), wires (2100), connectors (405), and controller-processor (2200). At least the working electrode is coated by an enzyme-coated sensing layer. Upon contact of the enzyme-coated layer with the surrounding fluid which contains glucose, electrons are generated within the sensing layer by virtue of an enzyme-catalyzed electrochemical reaction. The electrons are transferred by the electrodes and wires (2100), through the connectors (405), to the processor-controller (2200) and are detected therein as an electrical signal, the intensity of which is proportional to the glucose concentration. The sensing means (2000) and the tip (330) can be deployed in the disposable part (200) and the processor-controller (2200) can be located in the reusable part (100). In some embodiments, the electron-transferring wires and connectors can be embedded within the cradle unit (20) as will be further explained with reference to FIG. 26b.

FIGS. 12a-b shows an embodiment of a two-part patch unit (10) employing electrochemical-sensing when the electrodes are placed on the outer periphery of the tip (330). FIG. 12a shows a two-part patch unit (10) that is connected to cradle (20) which is adherable to the skin (5). The patch unit (10) includes the reusable part (100) and the disposable part (200). The monitoring apparatus (1006) includes processor-controller (2200) and connectors (405) in the reusable part (100), wiring (2100) and connectors (405) in the disposable part (200), and a tip (330) with electrodes (120, 121, and 122). In this embodiment, the electrodes (120, 121, 122) extend along the entire or partial outer periphery of the tip (330). FIG. 12b shows a cross-sectional view of the tip (330) with longitudinal electrodes (120, 121, 122) on its outer periphery.

FIGS. 13a-c shows an embodiment of a two-part patch unit (10) employing electrochemical sensing, in which the electrodes are located on the outer periphery of the tip (330) transversally, in a concentric, ring-like, manner. FIG. 13a shows the two-part patch unit (10) that is connected to cradle unit (20) which is adherable to the skin (5). The patch unit (10) comprises reusable (100) and disposable (200) part. The monitoring apparatus (1006) includes processor-controller (2200) and connectors (405) in the reusable part (100), wiring (2100) and connectors (405) in the disposable part (200) and tip (330) with electrodes (120, 121, 122). In this embodiment, the electrodes (120, 121, 122) are located on the outer periphery side of the tip (330) concentrically, in a ring-like manner. FIGS. 13b and 13c show longitudinal cross-sectional and isometric views, respectively, of the tip (330) with ring-like electrodes (120, 121, 122) transversally located on its outer periphery, and the electrical current transfer wiring (2100).

FIG. 14 shows a two-part patch unit (10) which includes the dispensing apparatus (1005) and the monitoring apparatus (1006), employing electrochemical monitoring. FIG. 14 shows the details of the monitoring apparatus (1006) within the reusable part (100) and disposable part (200). The patch unit (10) is connected to cradle unit (20) which is adherable to skin (5). The monitoring apparatus (1006) is shared between the reusable part (100) and disposable part (200) and employs an electrochemical sensing means (2000). The reusable part (100) includes processor-controller (2200) and an electric circuit (400). The circuit (400) contains necessary components to provide a potential or current to the electrodes for the electrochemical reaction that occurs on the electrodes, and to measure the electrical current or potential produced by the electrodes due to this electrochemical reaction. Wires (2100) and connectors (405) are provided to electrically connect between the disposable (200) and reusable (100) parts. The disposable part (200) is connected to a tip (330) which contains the sensing means (2000), located subcutaneously.

The dispensing apparatus (1005) can also be contained within the reusable part (100) and the disposable part (200), where the reusable part (100) includes the driving mechanism (114) and pumping mechanism (116), and the disposable part (200) includes reservoir (220) and delivery tube (230). Upon connection of the patch unit (10) to the tip (330), fluid can be delivered from the reservoir through the tip (330) into the body, and analytes within the body can be monitored.

Figure 15:
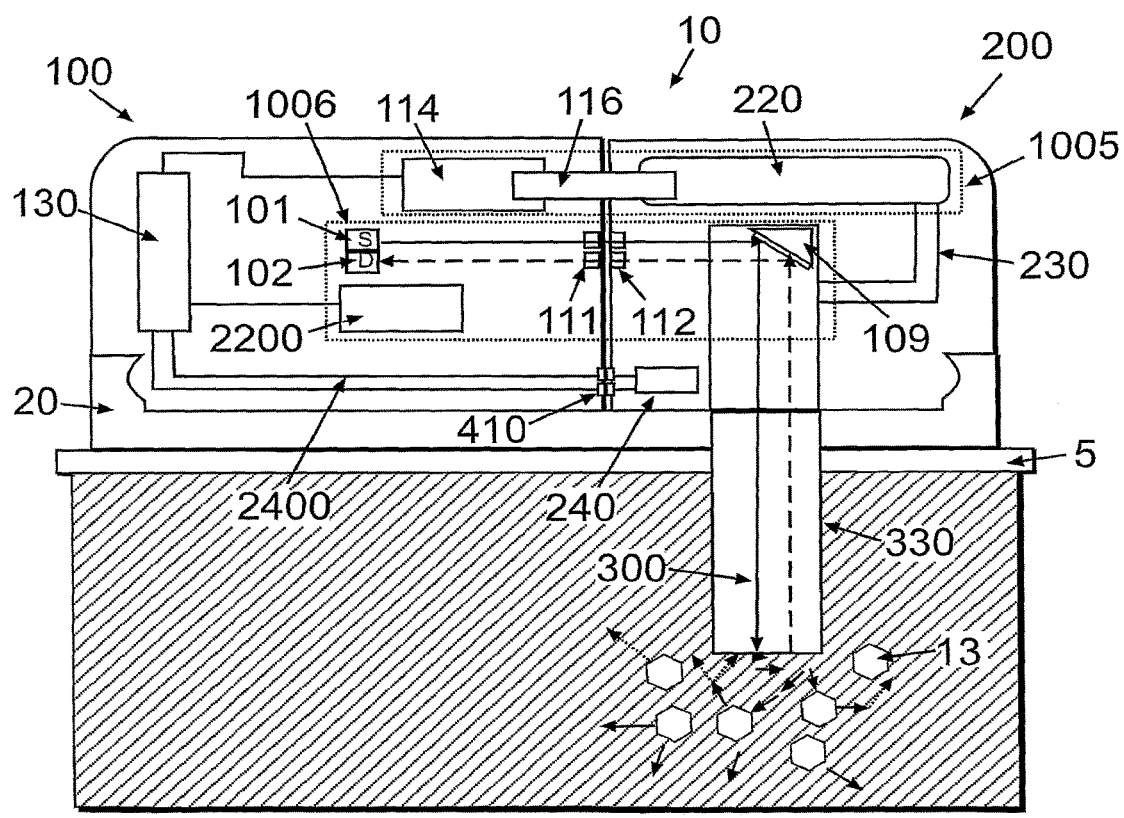
FIG. 15 illustrates in detail an embodiment of the two-part patch unit connected to the tip and employing an optical monitoring apparatus.

FIGS. 15-17 show embodiments of a two-part patch unit (10) which includes a dispensing apparatus (1005) employing a pumping mechanism (116) and a monitoring apparatus (1006) employing an optical sensing mechanism. The dispensing apparatus (1005) includes driving mechanism (114) and pumping mechanism (116), which are contained in the reusable part (100). The dispensing apparatus (1005) further includes reservoir (220), delivery tube (230), energy supply (240), and outlet port (not shown) contained in the disposable part (200). The electronics (130) and processor-controller (2200) are located in the reusable part (100) and can be used by both the dispensing apparatus (1005) and monitoring apparatus (1006). In some embodiments, the energy supply (240) can be located in the reusable part (100).

The monitoring apparatus (1006) in the shown embodiment includes at least one light-emitting source (101), at least one detector (102), and at least one optical deflecting means (109). The path of light propagating from the light-emitting source (101) into the body is shown as a solid line and the path of light propagating from the body to the detector (102) is shown as a dashed line. Emitted light (300) from the light-emitting source (101) is deflected by deflecting means (109) to the body and the returned light reaches the detector (102) and is analyzed by the processor-controller (2200). The light-emitting source (101), detector (102), and processor-controller (2200) can be located in the reusable part (100) and the deflecting means (109) can be located in the reusable part (100). Windows (111, 112) are provided in the reusable part (100) and disposable part (200). The windows (111, 112) are aligned and maintain passing of the light along the above paths after the reusable part (100) and disposable part (200) are paired.

FIG. 15 shows the two-part patch unit (10), connected to a cradle unit (20) which is adherable to skin (5) and the components of the optical-based monitoring apparatus (1006) which is divided between the reusable part (100) and disposable part (200). Light emitted from the source (101) is deflected by the deflecting means (109) to a tip (330) and into the ISF of the subcutaneous tissue. Spectra of the emitted light can be varied depending on the measured analyte (13). For example, if the analyte is glucose, a spectra in the near-infrared (NIR), mid infrared, or visible light range can be used (altogether or separately). The light (300) propagating towards the tip's (330) distal end returns to the tip (330), and then, via the deflecting means (109), to the detector (102). The reflected light spectra are analyzed by the processor-controller (2200) to obtain analyte concentration levels. Embodiments of patch units (10) with various configurations for directing light from the light-emitting source (101) through the tip (330) to the body and then back to the detector (102), are discussed in U.S. Provisional Patent Application No. 61/004,039, the disclosure of which is incorporated herein by reference in its entirety.

FIGS. 16a-17c illustrate embodiments of the two-part patch unit (10) having a dispensing apparatus (1005) and a monitoring apparatus (1006). The dispensing apparatus (1005) includes the driving and pumping mechanisms (not shown in FIGS. 16a-17c) in the reusable part (100), and reservoir (220) and delivery tube (230) in the disposable part (200). The dispensing apparatus (1005) delivers fluid from the reservoir (220) through the delivery tube (230) via the pumping mechanism (not shown in FIGS. 16a-17c) through the tip (330) to the body. The monitoring apparatus (1006) contains light-emitting source (101) and detector (102) located in the reusable part (100), optical fiber (106) and lens (105) which can be located in the reusable part (100) or disposable part (200). Deflecting means (109) can include a reflecting mirror (108), which directs the light (300) to and from the body. In some embodiments, an additional optical coupler (190) may be present between the reusable (100) and disposable (200) parts, and/or at the distal end of the tip (330). The optical coupler (190) may include without limitation a window inclined at a certain angle (e.g., 8 degrees) to ensure that reflected light is not coupled back from the tissue to the optical fiber (106).

Figure 16A:
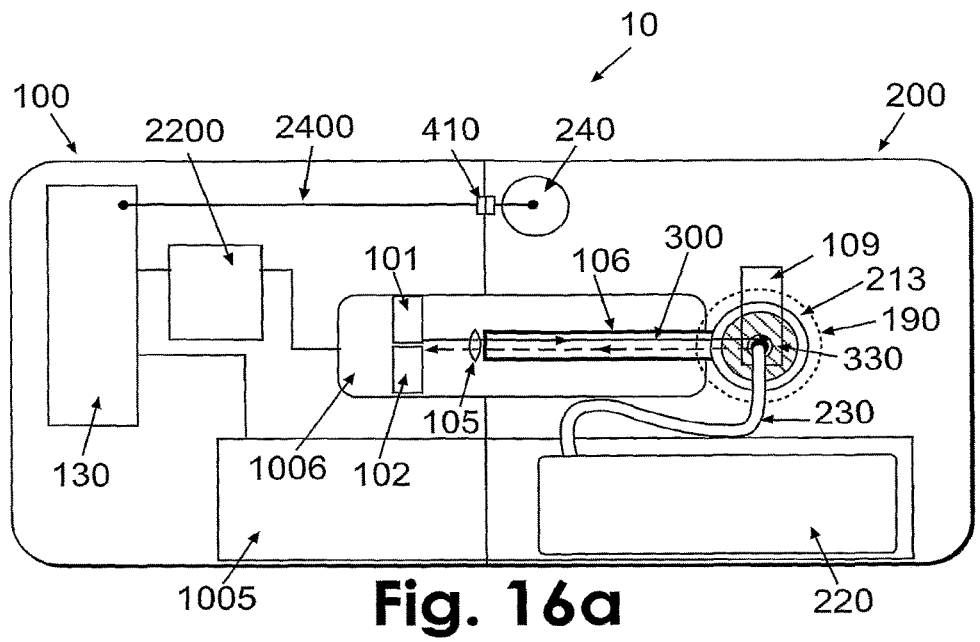
FIGS. 16a-c show, respectively a top view, cross-sectional view, and enlarged view of an embodiment of a two-part patch unit employing optical monitoring apparatus.
Figure 16B:
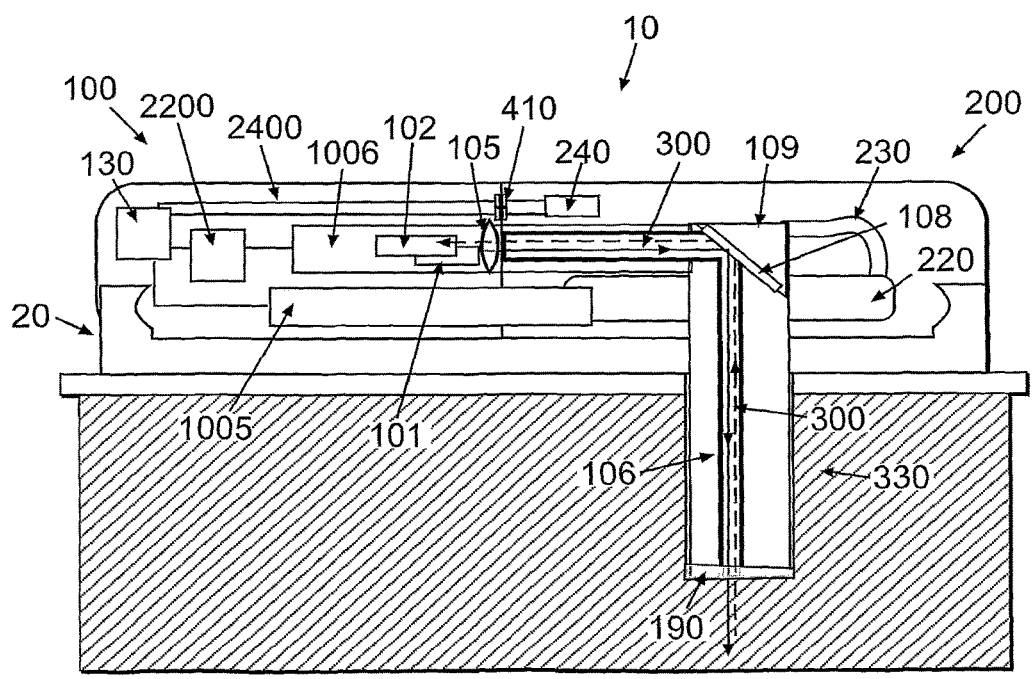
Figure 16C:
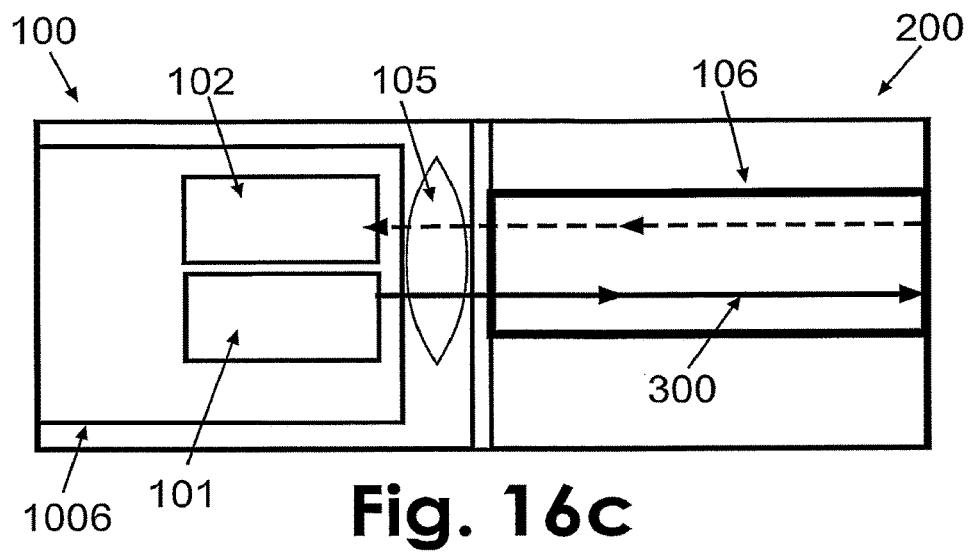

FIGS. 16a-c show an embodiment of the two-part patch unit (10) comprising dispensing apparatus (1005) and monitoring apparatus (1006). The monitoring apparatus (1006) includes lens (105), for focusing the light (300) passing between the reusable part (100) and disposable part (200). In some embodiments, the optical lens (105) serves as collimating means, or focusing means, for narrowing down the scattering of the emitted and returning light. The lens may be made from a variety of suitable materials, including without limitation, plastic, glass, or crystal. Use of a plastic lens may be more cost-effective; however, glass and crystal have superior optical properties.

FIG. 16a and FIG. 16b show a side-view and a top-view, respectively, of the patch unit (10) with the lens (105) located between the reusable and disposable parts (100, 200). FIG. 16c shows an enlarge view of the contact surfaces between the reusable part (100) and disposable part (200) and the passage of light (300) between the two parts via the lens (105).

Figure 17A:
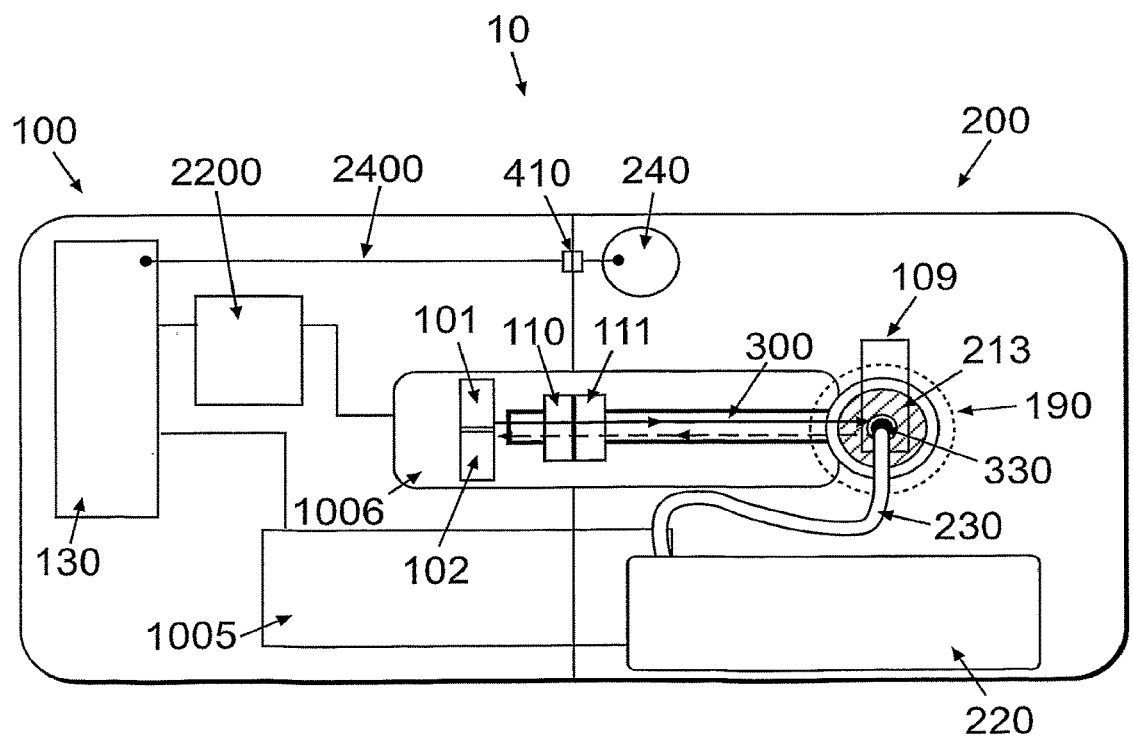
FIGS. 17a-c show, respectively a top view, cross-sectional view, and enlarged view of an exemplary two-part patch unit employing optical monitoring apparatus having two optical windows.
Figure 17B:
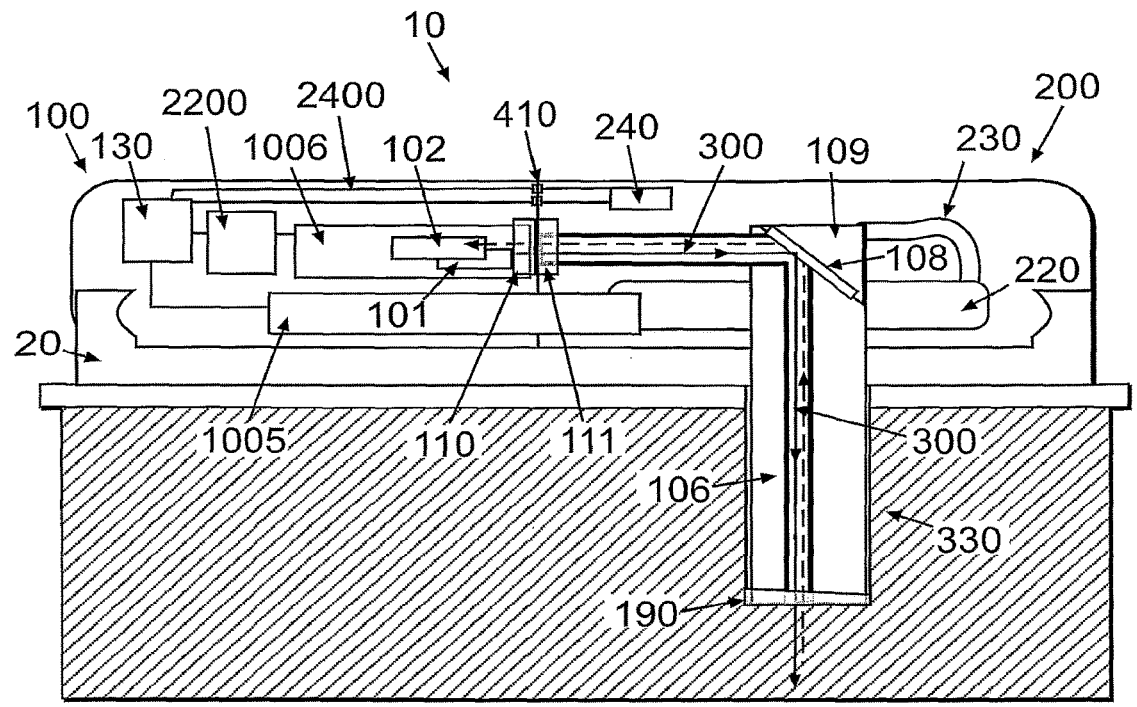
Figure 17C:
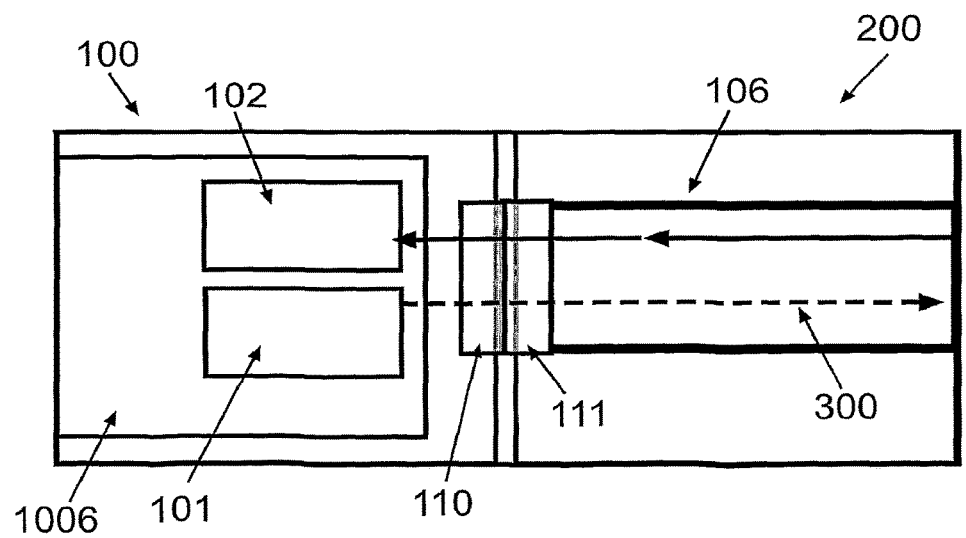

FIGS. 17a-c show a side-view (FIG. 17a) and a top-view (FIG. 17b) of the two-part patch unit (10) having a dispensing apparatus. (1005) and a monitoring apparatus (1006). The light path through the monitoring apparatus (1006) includes two aligned optical windows (110, 111) located in the reusable part (100) and disposable part (200), respectively, and enabling passage of light (300) between the two parts. The optical windows (110, 111) serve as means for allowing the passage of light (300) between the reusable (100) and disposable (200) parts. FIG. 17c shows direction (300) of light passing between the reusable part (100) and disposable part (200) and going through optical fibers (106) and the two optical windows (110, 111). In some embodiments, the two windows (110, 111) may be, both or separately, inclined by for example, about an eight-degree angle to prevent backwards optical reflection into the optical fiber (106). In other embodiments, the two optical windows (110, 111) are made of material, which is translucent to light in the wavelengths relevant for detecting analyte concentration levels, allowing for light to pass through the windows (110, 111). The windows (110, 111) can be made from a variety of suitable materials, including without limitation, plastic, glass, or crystal. In some embodiments, the optical windows (110, 111) serve as focusing means, so that when the emitted or returned light passes through them, they narrow down any possible scattering of the light.

The monitoring apparatus (1006) can use any one of the following optical means:

Near-Infrared (NIR) spectroscopy: NIR transmission and reflectance measurements of glucose are based on the fact that glucose-specific properties are embedded within the NIR spectra and can be extracted by using multivariate analysis methods (Diab Tech Ther 2004; 6(5): 660-697, Anal. Chem. 2005, 77: 4587-4594).

Mid-IR spectroscopy: This range contains absorbance fingerprints generated by the highly specific and distinctive fundamental vibrations of biologically important molecules such as glucose, proteins, and water. Two strong bands of glucose are found at 9.25 inn and 9.65 1.1, M.

Light scattering: Light scattering is measured by a localized reflectance (spatially resolved diffuse reflectance) or NIR frequency domain reflectance techniques. In the localized reflectance, a narrow beam of light illuminates a restricted area on the surface of a body part, and reflected signals are measured at several distances from the illumination point. Both localized reflectance measurements and frequency domain measurements are based on changes in glucose concentration, which affects the refractive index mismatch between the ISF and tissue fibers.

Raman spectroscopy: The Raman Effect is a fundamental process in which energy is exchanged between light and matter. In Raman spectroscopy, the incident light, often referred to as 'excitation' light, excites the molecules into vibration motion. Since light energy is proportional to frequency, the frequency change of this scattered light must equal the vibration frequency of the scattering molecules. This process of energy exchange between scattering molecules and incident light is known as the Raman Effect. The Raman scattered light can be collected by a spectrometer and displayed as a 'spectrum', in which its intensity is displayed as a function of its frequency change. Since each molecular species has its own unique set of molecular vibrations, the Raman spectrum of a particular species will consist of a series of peaks or 'bands', each shifted by one of the characteristic vibration frequencies of that molecule. Thus, Raman spectroscopy can be employed to accurately measure tissue and blood concentrations of glucose (Phys. Med. Biol. 2000 45 (2) R1-R59).

Fluorescence energy transfer (FRET)-based assay: Concanavalin A is labeled with the highly NIR-fluorescent protein allophycocyanin as donor and dextran labeled with malachite green as the acceptor (J Photochem Photobiol 2000; 54: 26-34; Anal Biochem 2001; 292: 216-221). Competitive displacement of the dextran from binding to the lectin occurs when there are increasing glucose concentrations, leading to a reduction in FRET, measured as intensity or lifetime (time-correlated single-photon counting).

Photoacoustic method: Photoacoustics ("PA") involves ultrasonic waves created by the absorption of light. A medium is excited by a laser pulse at a wavelength that is absorbed by a particular molecular species in the medium. Light absorption and subsequent radiationless decay cause microscopic localized heating in the medium, which generates an ultrasound pressure wave that is detectable by a hydrophone or a piezoelectric device. Analysis of the acoustic signals can map the depth profile of the absorbance of light in the medium. Glucose trends can be tracked by the photoacoustic technique which can work as a noninvasive instrument for the monitoring of blood glucose concentrations (Clin Chem 1999 45(9): 1587-95).

Figure 18:
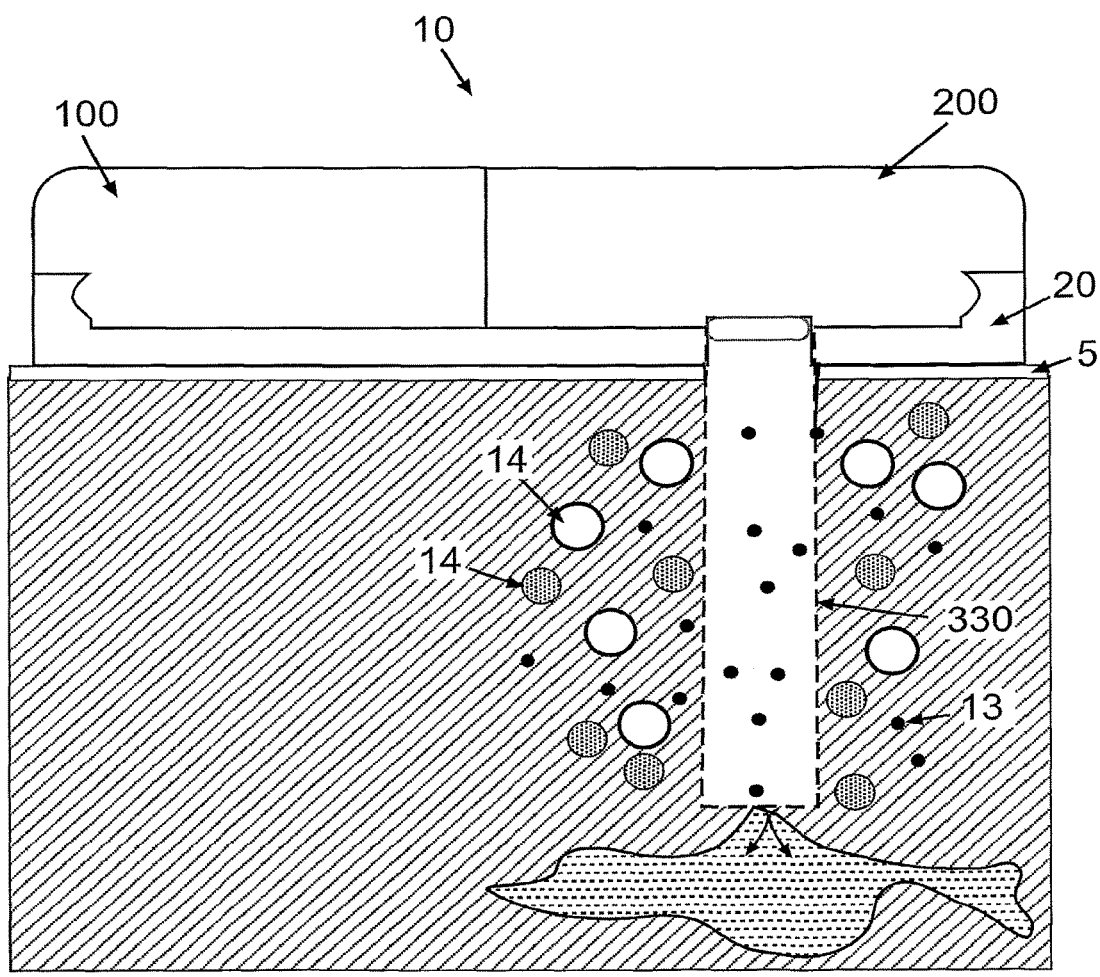
FIG. 18 shows the patch unit being connected to a semi-permeable cannula and the diffusion process.
Figure 19:
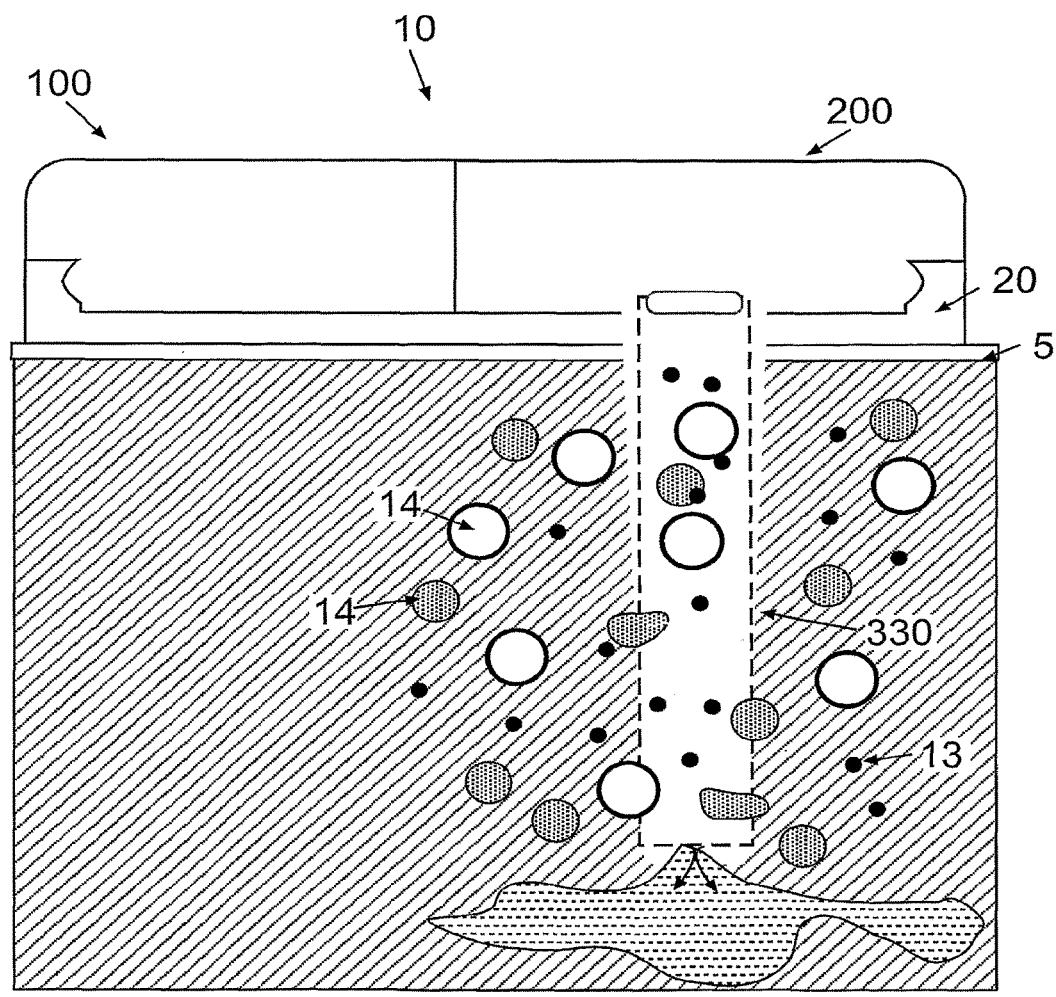
FIG. 19 shows the patch unit being connected to a permeable cannula and the diffusion process.

FIGS. 18-19 show embodiments of the two-part patch unit (10) having a reusable part (100) and a disposable part (200). The patch unit (10) is connected to cradle unit (20) which is adherable to the skin (5). The patch unit (10) contains dispensing and monitoring apparatuses (not shown in FIGS. 18-19) that use tip (330). In the shown embodiments, the tip (330) is semipermeable or permeable, allowing for diffusion of analyte molecules into the tip (330) across its membrane wall. The dispensed fluid (e.g., insulin) is used as a solution within the tip (330) into which molecules from the surrounding ISF can diffuse. Diffusion of analyte molecules across the semi-permeable or permeable membrane follows the direction of the concentration gradient. The analyte concentration within the tip (330) is proportional or equal to the analyte concentration in the surrounding ISF depending on the recovery time, which is defined as the time for achieving concentration equilibrium.

FIG. 18 shows an embodiment of the patch unit (10) that is connected to the single subcutaneously insertable tip (330). The tip (330) includes a semi-permeable membrane allowing diffusion of low molecular weight molecules (13) (e.g., glucose) while providing a barrier for high molecular weight molecules (14).

FIG. 19 shows an embodiment in which the tip (330) includes a permeable membrane which is permeable for both small molecular weight molecules (13) and large molecular weight (14) molecules. The permeable tip can be cheaper and allows rapid recovery time but renders specific analyte (usually consisting of small molecular weight molecules) monitoring less accurate.

In some embodiments, the tip (330) that is used for monitoring analyte concentration levels and for delivering fluid is a microdialysis ("MD") or a microperfusion ("MP") probe, as known in the art. The probe may be perfused with the dispensed fluid (e.g., insulin), or with an additional/alternative perfusion fluid (e.g., saline). The tip membrane may be either semipermeable or permeable. MD probes are known in the art and examples of their description can be found in U.S. Pat. No. 4,694,832 to Ungerstedt, as well as from the document of CMA/Microdialysis AB Company, under the name "CMA 60 Microdialysis Catheter" or "CMA 70 Brain Microdialysis Catheters". An MD probe coupled with a cannula for insertion is also discussed in the published U.S. Pub. No. 2005/0119588 to Model et al.

Figure 20A:
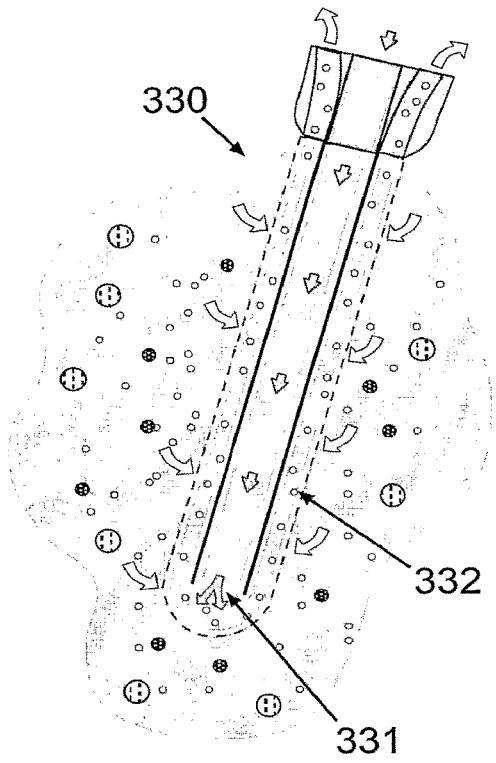
FIGS. 20a-b show the patch unit being provided, respectively, with a tip for Microdialysis or for Microperfusion.
Figure 20B:
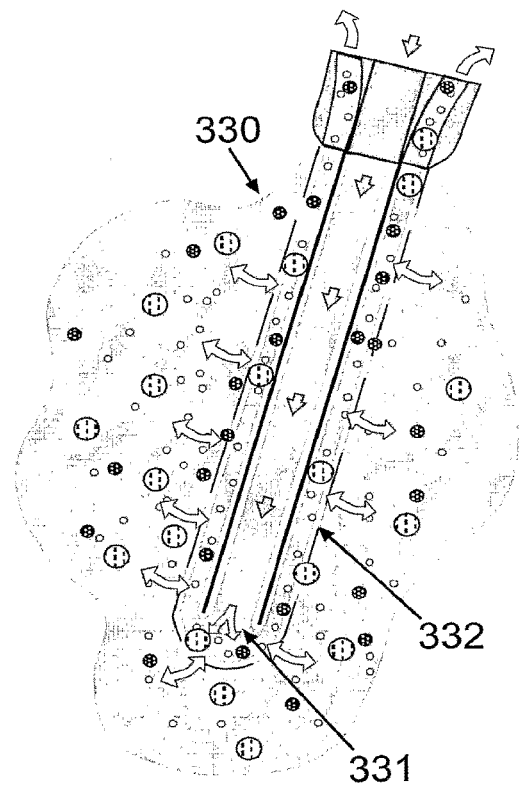

FIGS. 20a-b show embodiments of the tip (330), in which the MD tip (FIG. 20a) or the MP tip (FIG. 20b) is used and which is similar to MD or MP probes known by those of ordinary skill in the art, apart from the fact that it contains an opening at the bottom (331), or on its side (332), allowing for fluid entering the tip (33) to be delivered via the tip (330) from the patch unit (10) to the user's body. Thus, the tip (330) in this embodiment, serves both as a means for dispensing fluid into the body and as a MD or MP probe for monitoring analyte concentrations.

In embodiments which are based on molecular diffusion and the tip (330) is semi-permeable or permeable, the analyte sensing means can be configured in one of the following configurations:
1. Intrinsic configuration—the sensing means reside at the tip and is located in the subcutaneous compartment.
2. Extrinsic configuration—the sensing means reside within the patch unit being located outside the subcutaneous compartment. The analyte-rich fluid can be transferred to the patch unit, where analyte concentration sensing can be performed outside the body. In this configuration, the dispensing apparatus contains means for transferring of analyte rich fluid from the distal end of the tip, which is located subcutaneously to the proximal end of the tip that is located within the patch (e.g., by reversing the direction of fluid delivery).

Analyte sensing means can be based on electrochemical, optical, acoustic, or any other analyte sensing means known by those of ordinary skill in the art.

Figure 21A:
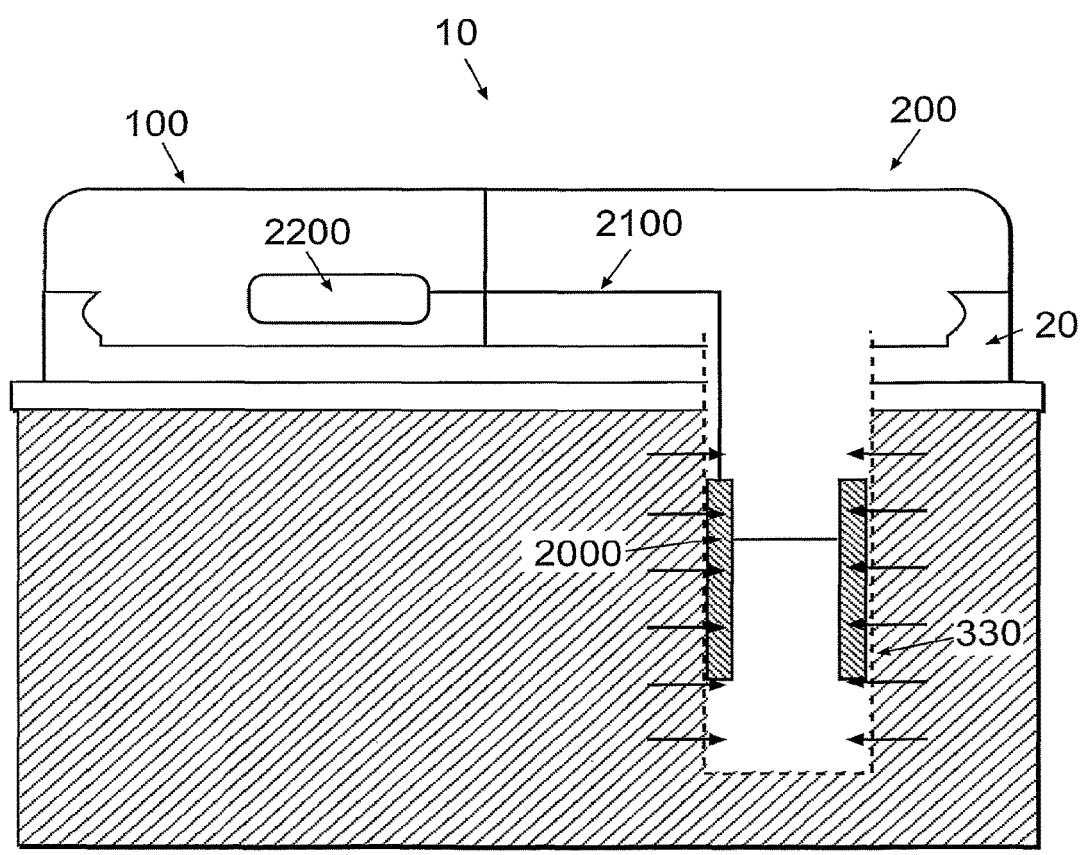
FIGS. 21a-b show an embodiment of a two-part patch unit employing electro-chemical monitoring apparatus with either extrinsic or intrinsic sensing means.
Figure 21B:
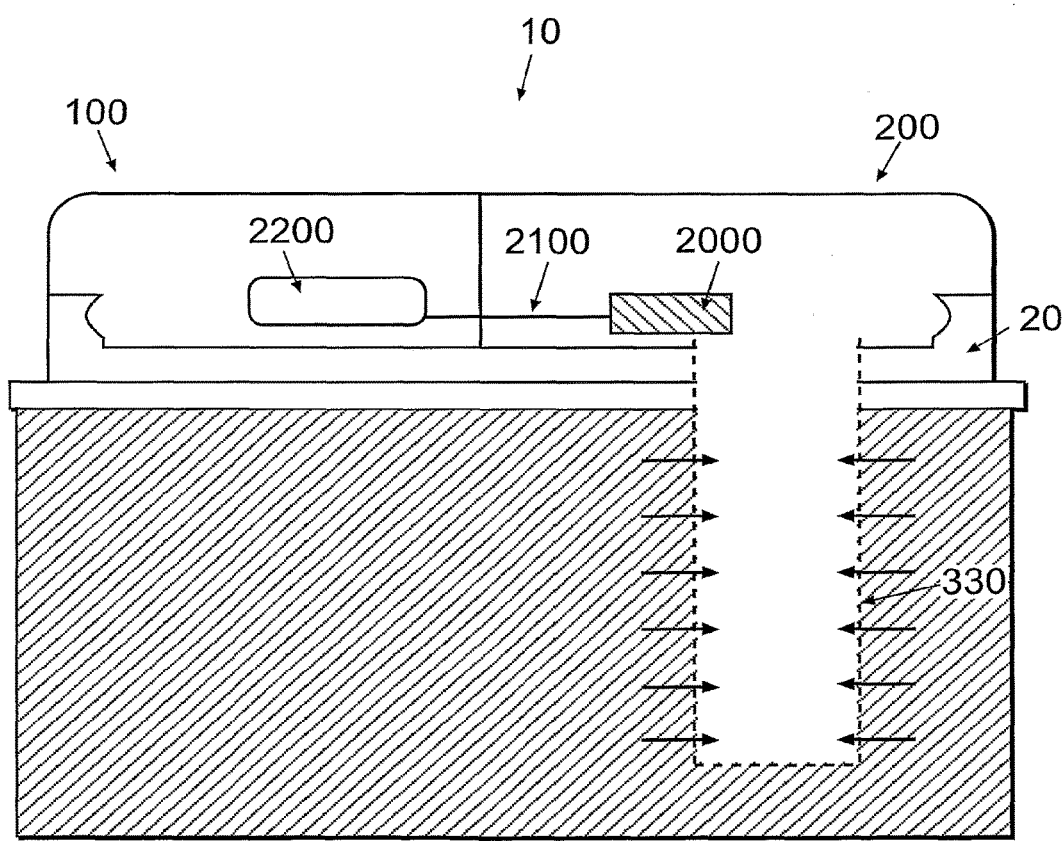

FIGS. 21a-b show a two-part patch unit (10) having reusable (100) and disposable (200) parts. The patch unit (10) contains a dispensing apparatus and a electrochemical monitoring apparatus, and is connected to a cradle unit (20). The patch unit (10) can be connected to tip (330) having a membrane which is semi-permeable or permeable. The monitoring apparatus is provided with sensing means (2000). FIGS. 21a and 21b show two configurations of the sensing means (2000) within the tip (i.e., intrinsic) (FIG. 21a) and within the patch (i.e., extrinsic) (FIG. 21b).

FIG. 21a shows an embodiment of a two-part patch unit (10) that includes dispensing and monitoring apparatuses (not shown in FIGS. 21a-b), which employs an intrinsic sensing means (2000). The patch unit (10) is connected to cradle (20) that is adherable to skin (5). The monitoring apparatus includes processor-controller (2200) located in the reusable part (100), wires (2100) located in reusable and disposable parts (100 and 200), and tip (330) with sensing means (2000). The sensing means (2000) is located within the tip (330) (intrinsic configuration). The tip (330) has a permeable or semi-permeable membrane that allows analyte to diffuse in the direction of the concentration gradient (illustrated by arrows).

FIG. 21b shows an embodiment of a two-part patch unit (10) that includes dispensing and monitoring apparatuses (not shown in FIG. 21b) which employs an extrinsic sensing means. The patch unit (10) is connected to cradle unit (20) that is adherable to skin (5). The monitoring apparatus includes processor-controller (2200) located in the reusable part (100), wires (2100) located in the disposable part (200), and tip (330). The sensing means (2000) is located within the patch (10), preferably in the disposable part (200) (extrinsic configuration). The tip (330) has permeable or semi-permeable membrane that allows analyte molecules to diffuse in the direction of the concentration gradient (shown by arrows). The dispensing apparatus contains means (not shown) for transferring analyte-rich fluid from the tip (330) into the patch unit (10). One method of such transfer includes reversing the direction of fluid delivery, as disclosed in the co-owned, co-pending International Patent Application No. PCT/US08/062928 and U.S. patent application Ser. No. 12/116,546, both of which claim priority to U.S. Provisional Patent Application No. 60/928,054, the disclosures of which are incorporated herein by reference in their entireties.

FIGS. 22a-c and 23 show embodiments of a two-part patch unit (10) that includes a dispensing apparatus (1005) and an electrochemical monitoring apparatus (1006). The patch unit (10) includes a reusable part (100) and a disposable part (200) and is connected to cradle unit (20), which is adherable to the skin (5). The dispensing apparatus (1005) includes processor-controller (2200), driving mechanism (114) and pumping mechanism (116), located in the reusable part (100), and reservoir (220) and delivery tube (230), located in the disposable part (200). The monitoring apparatus (1006) includes the processor-controller (2200) located in the reusable part (100), wires (2100), connectors (405), and electrochemical sensing means, which can be intrinsic or extrinsic.

Figure 22A:
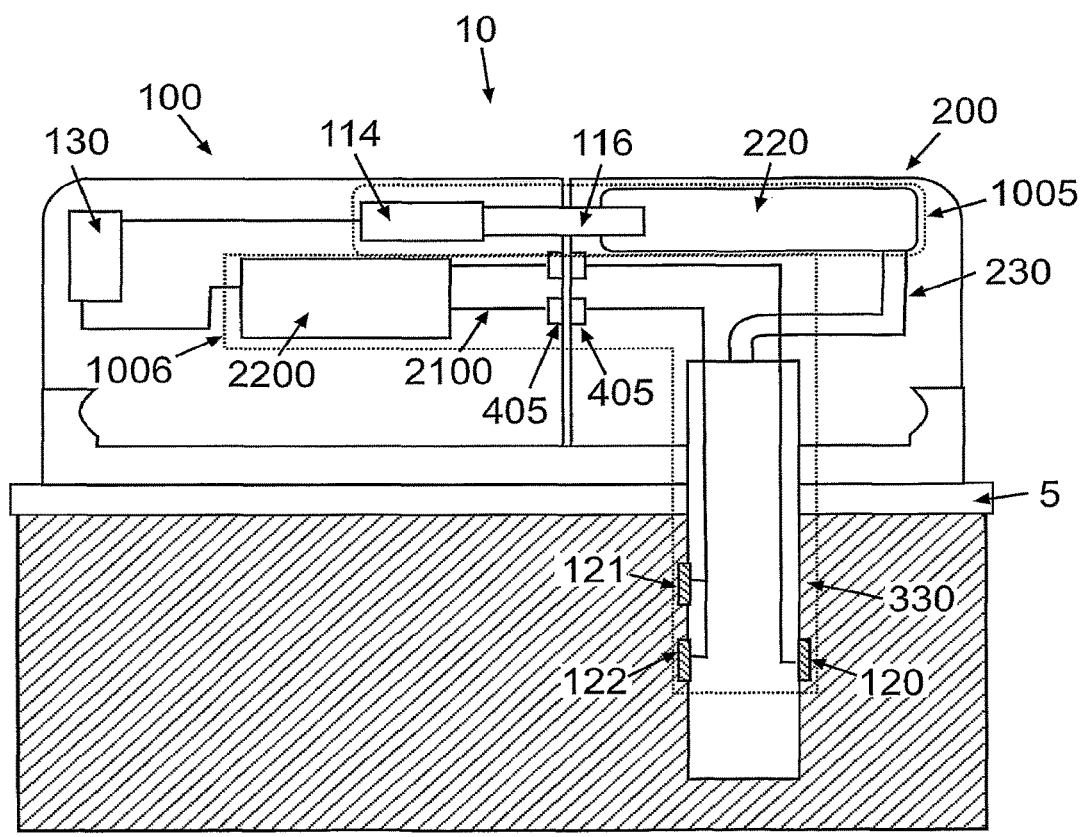
FIGS. 22a-c show an embodiment of a two-part patch unit containing an electro-chemical monitoring apparatus that employs an intrinsic sensing means.

FIG. 22a shows an exemplary embodiment of an electrochemical-based monitoring apparatus (1006) that contains an intrinsic configuration of a sensing means. The sensing means is located on the tip (330) in the subcutaneous compartment and includes a working electrode (120), counter electrode (121), and reference electrode (122). The electrodes can be located longitudinally on the outer or inner side of the tip. Current is transferred from electrodes by wires (2100) and connectors (405) to the processor-controller (2200).

Figure 22B:
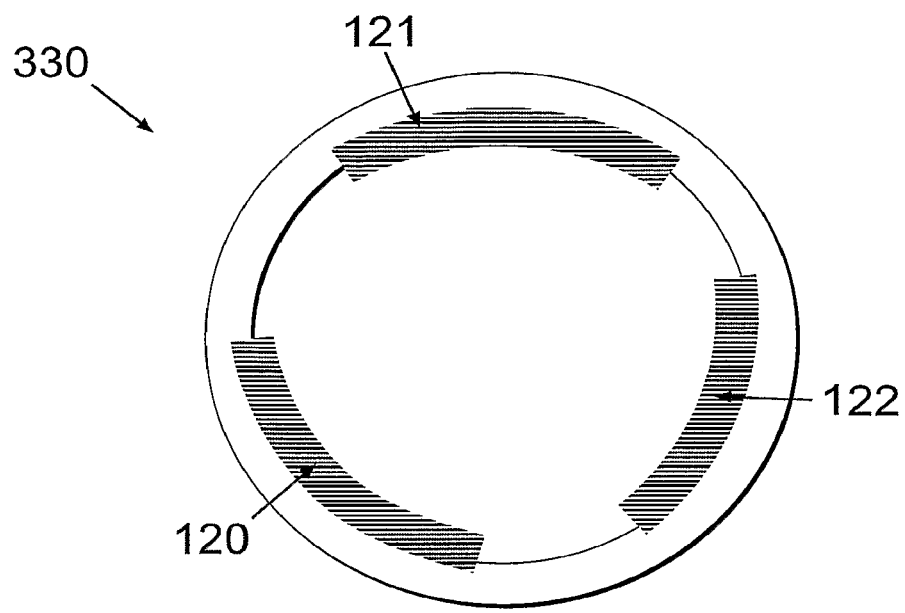
Figure 22C:
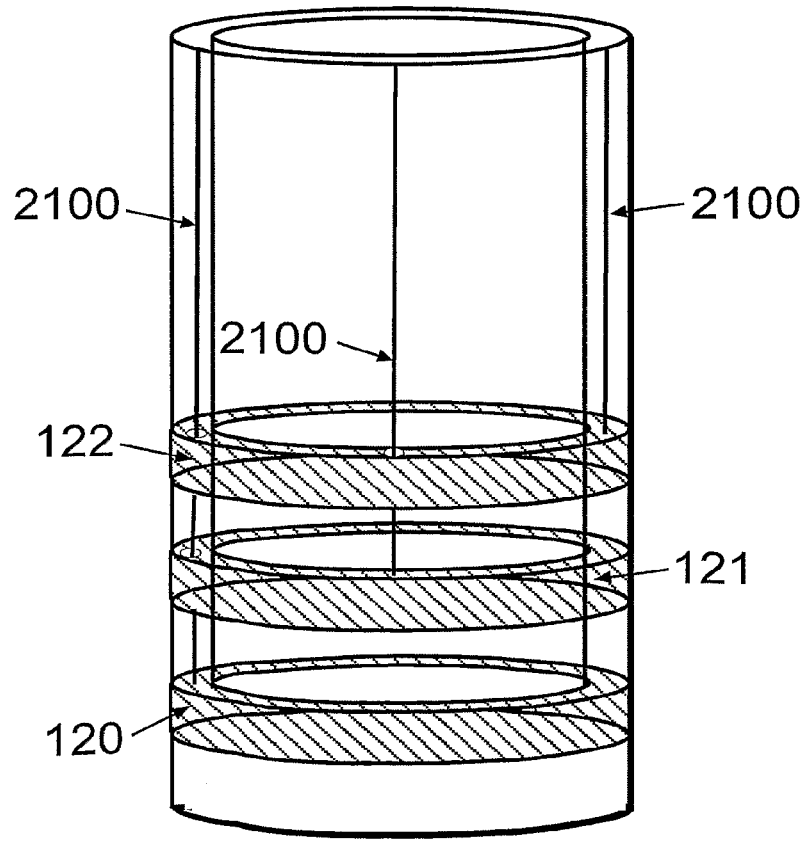

FIGS. 22b and 22c show a transverse cross-sectional view (FIG. 22b) and isometric view (FIG. 22c) of concentrically, ring-like, electrodes (120, 121, 122) located transversally on the inner side of the tip (330). In the shown embodiment, the tip (330) is either permeable or semi-permeable. In some embodiments, the electrodes can be located on the outer side of the tip (330). The tip (330) may be circular, oval, rectangular, have a flat outer contour, or any other shape. The tip (330) may be non-permeable or semi-permeable and the electrodes can be located on the outer or inner surface of the tip (330).

Figure 23:
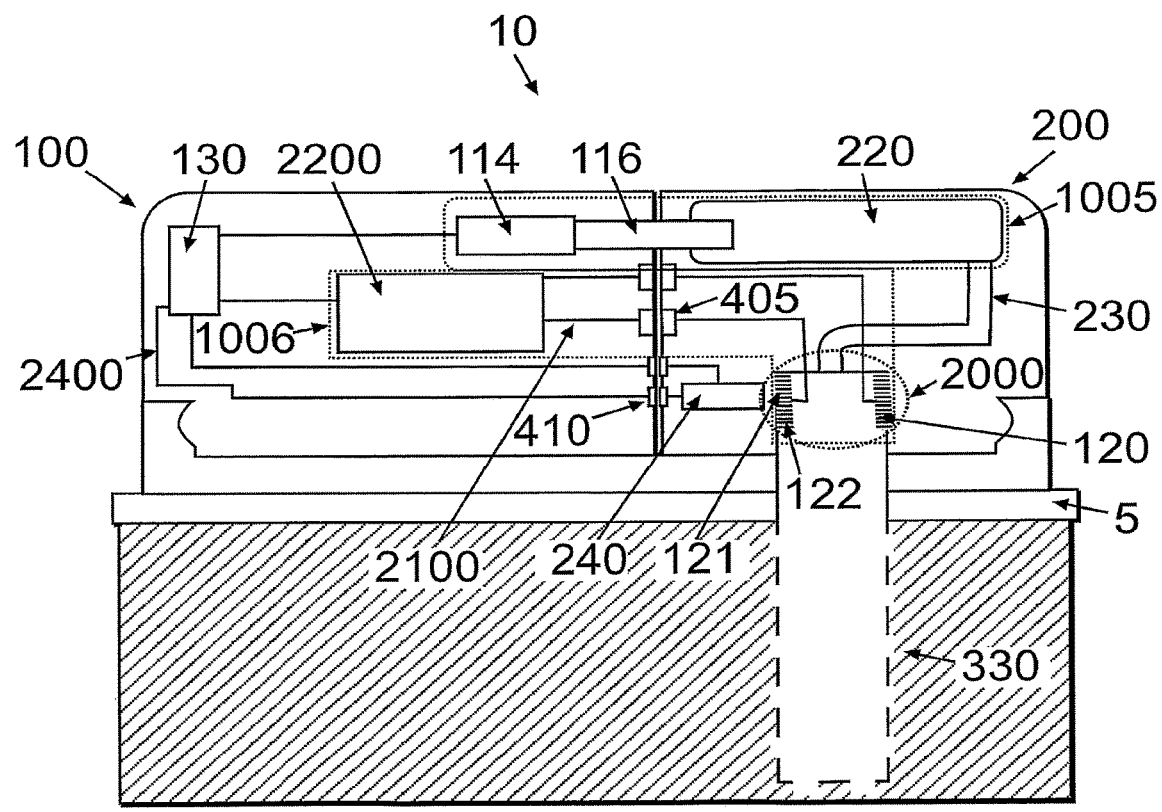
FIG. 23 shows an embodiment of a two-part patch unit containing an electro-chemical monitoring apparatus that employs an extrinsic sensing means.

FIG. 23 shows an embodiment of an electrochemical-based monitoring apparatus (1006) that contains extrinsic sensing means. Sensing means (2000) is located on the tip (330) within the patch unit (10) and can include at least one working electrode (120), counter electrode (121) or reference electrode (122). The electrodes can be located on the outer or inner surface of the tip (330). Current is transfer from electrodes by wires (2100) and connectors (405) to the processor-controller (2200). Analyte-rich solution from the subcutaneous tip portion (distal end of the tip) can reach the sensing means (proximal end of the tip) by diffusion along the tip (following the concentration gradient within the tip) or by forcible fluid transfer (e.g., due to reverse flow of the fluid within the tip created by reversing the pumping mechanism direction).

Figure 24:
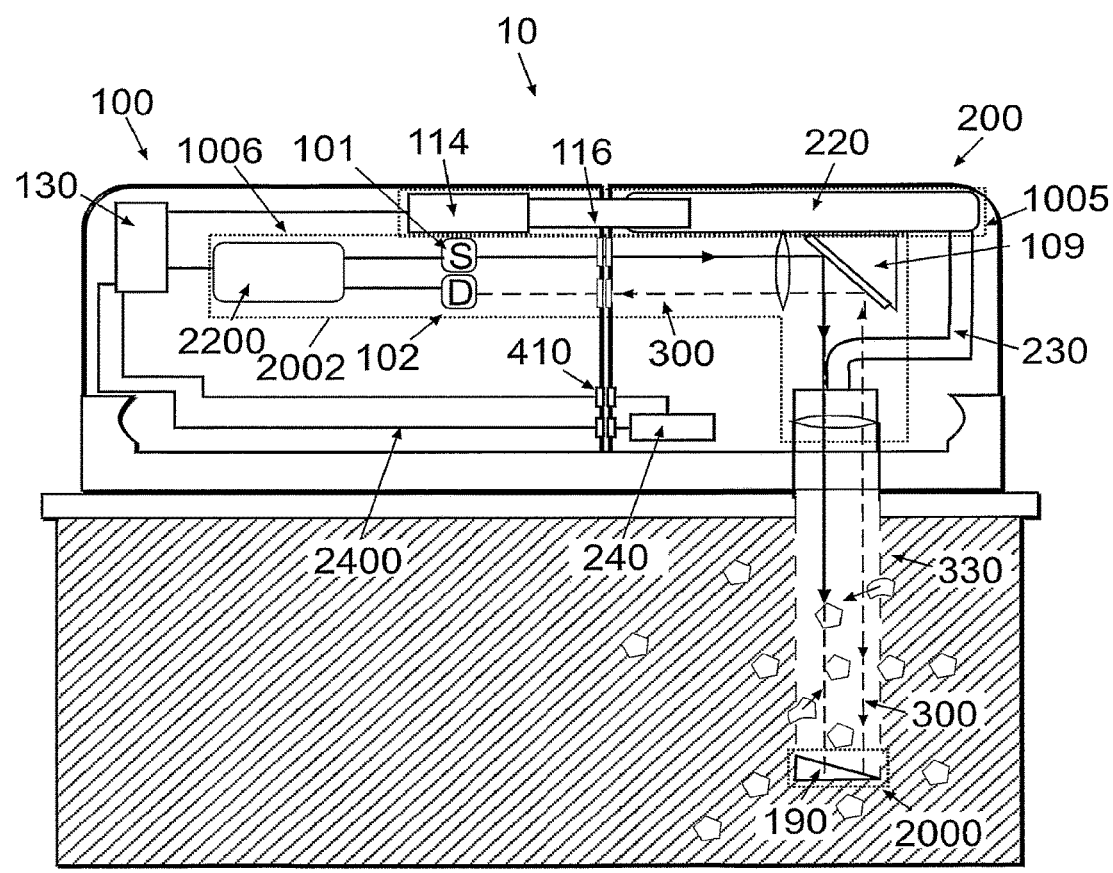
FIG. 24 shows an embodiment of a two-part patch unit employing an optically-based monitoring apparatus and intrinsic configuration of sensing means.
Figure 25:
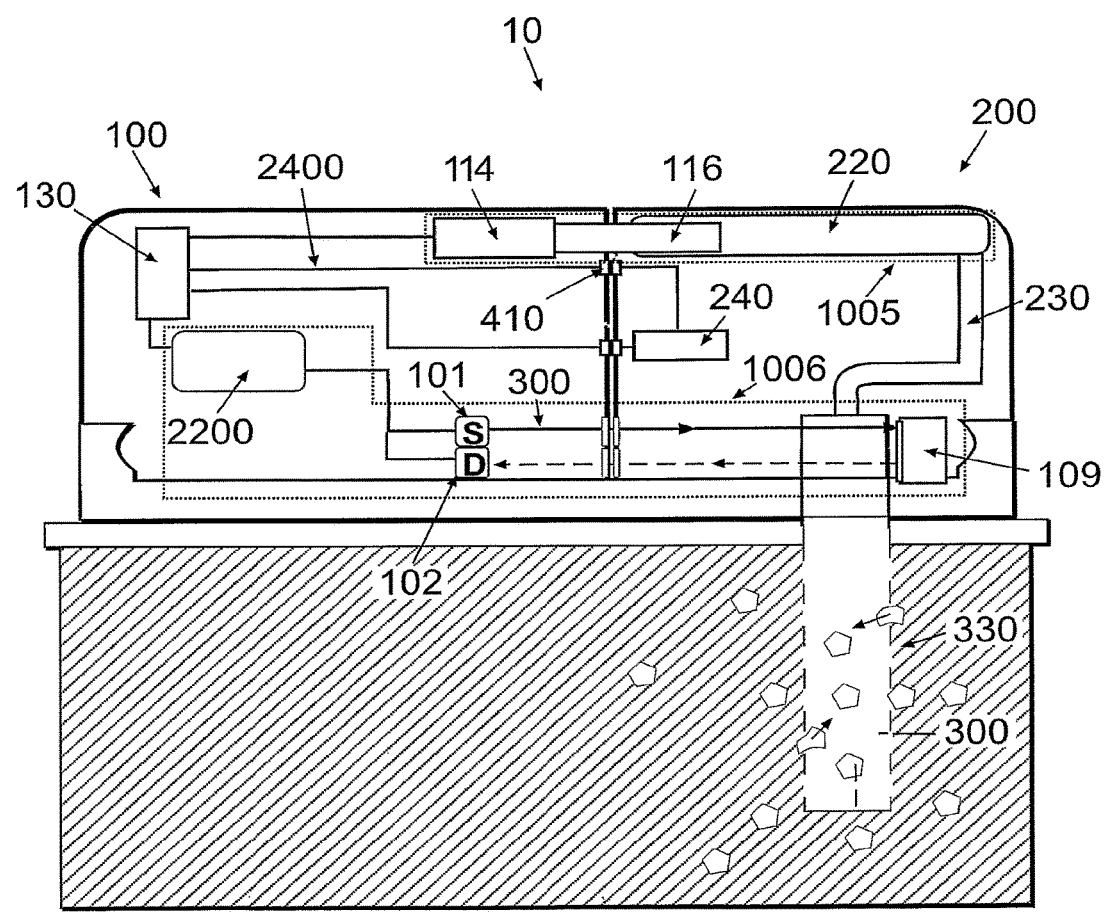
FIG. 25 shows an embodiment of a two-part patch unit employing an optical monitoring apparatus and extrinsic sensing means.

FIGS. 24-25 show embodiments of a two-part patch unit (10) that includes a dispensing apparatus (1005) and an optical-based monitoring apparatus (1006). The patch unit (10) includes reusable part (100) and disposable part (200) and is connected to cradle unit (20), which is adherable to the skin (5). The dispensing apparatus (1005) includes processor-controller (2200), driving mechanism (114) and pumping mechanism (116) located in the reusable part (100), and reservoir (220) and delivery tube (230) located in the disposable part (200). The monitoring apparatus (1006) includes light-emitting source (101), detector (102), and processor-controller (2200), located in the reusable part (100), wires (2100) and connectors (405) located in both parts. The tip (330) can be permeable or semi-permeable. The optical sensing means can be either intrinsic (FIG. 24) or extrinsic (FIG. 25). Optical means, e.g., windows, lens, may be deployed between the reusable (100) and disposable (200) parts for more efficient passage of light (300) between the two parts.

FIG. 24 shows an embodiment of two-part patch unit (10) that includes a dispensing apparatus (1005) and monitoring apparatus (1006). The dispensing apparatus (1005) includes processor-controller (2200), driving mechanism (114) and pumping mechanism (116) located in the reusable part (100), and reservoir (220) and delivery tube (230) located in the disposable part (200). The optical-based monitoring apparatus (1006) contains an intrinsic sensing means (2002). The sensing mechanism, including the light-emitting source (101) and detector (102), is located within the patch unit (10), and the sensing means (2000) is located in the tip (330). The sensing means (2000) resides in the subcutaneous compartment and includes at least one reflecting mirror (190). Direction (300) of light emitted from the source (101) is deflected by deflecting means (109) into tip (330) and the light is reflected by mirror (190) towards the deflecting means (109) and detector (102), to be analyzed by the processor-controller (2200). The tip (330) can be permeable or semi-permeable, thus the analyte of interest (i.e., glucose) can flow in the direction of the concentration gradient. Optical spectral analysis can be achieved when light passes through the analyte-rich solution within the tip (330).

FIG. 25 shows an embodiment of a two-part patch unit (10) that includes a dispensing apparatus (1005) and a monitoring apparatus (1006). The dispensing apparatus (1005) includes processor-controller (2200), driving mechanism (114) and pumping mechanism (116), located in the reusable part (100), and reservoir (220) and delivery tube (230), located in the disposable part (200). The optical-based monitoring apparatus (1006) contains an extrinsic sensing means. Some elements of the sensing means, including the light-emitting source (101) and detector (102) are located within the patch unit (10). Direction (300) of light (300) emitted from source (101) is directed towards the analyte-rich fluid, and is reflected by mirror (109) back to detector (102), to be analyzed by the processor-controller (2200). The tip (330) can be permeable or semipermeable, thus the analyte of interest (e.g., glucose) can flow in direction of the concentration gradient. Optical spectral analysis can be achieved when light passes through the analyte-rich solution within the tip (330). Analyte-rich solution from the subcutaneous tip portion (distal end of tip) can reach the sensing means within the patch unit (10) for sensing (proximal end of cannula) either by diffusion along the tip (330) (following the concentration gradient) or by active fluid transfer (e.g., due to backward flow of the fluid within the tip created by reversing the direction of movement of the pumping mechanism).

Figure 26A:
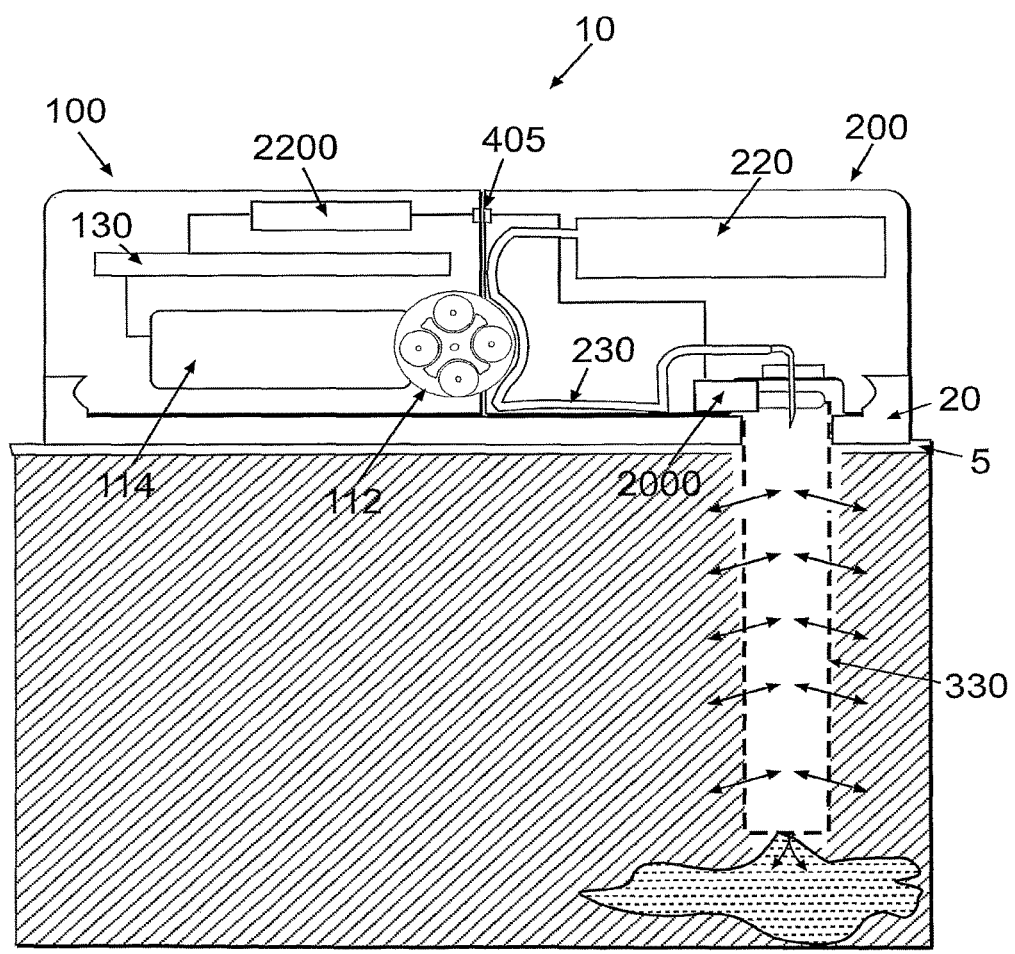
FIGS. 26a-b show an embodiment of a two-part patch unit employing extrinsic sensing means of the monitoring apparatus and means for transporting the fluid rich analyte from the tip distal end (within the subcutaneous tissue) towards the proximal end within the patch unit.

FIG. 26a shows an embodiment of a patch unit (10) that contains a dispensing apparatus and monitoring apparatus. The monitoring apparatus contains an extrinsic sensing means (2000) wired to a processor-controller (2200) connected to the electronic components (130). The dispensing apparatus employs driving mechanism (114) and a peristaltic pumping mechanism composed of a rotary wheel (112), which dispenses fluid in the direction of rotation (clockwise or counter clockwise) from the reservoir (220) via a delivery tube (230). Accordingly, flow can be delivered forward (from patch unit (10) to tip (330)) and backward (form tip (330) to patch unit (10)). The monitoring apparatus can employ electrochemical or optical sensing. Delivery of analyte-rich fluid from the distal end of the tip (330) to the proximal end within the patch unit (10) brings to the sensing means (2000) within the patch unit (10) a solution which contains analyte concentration identical (or at a known ratio) to that in the ISF.

Figure 26B:
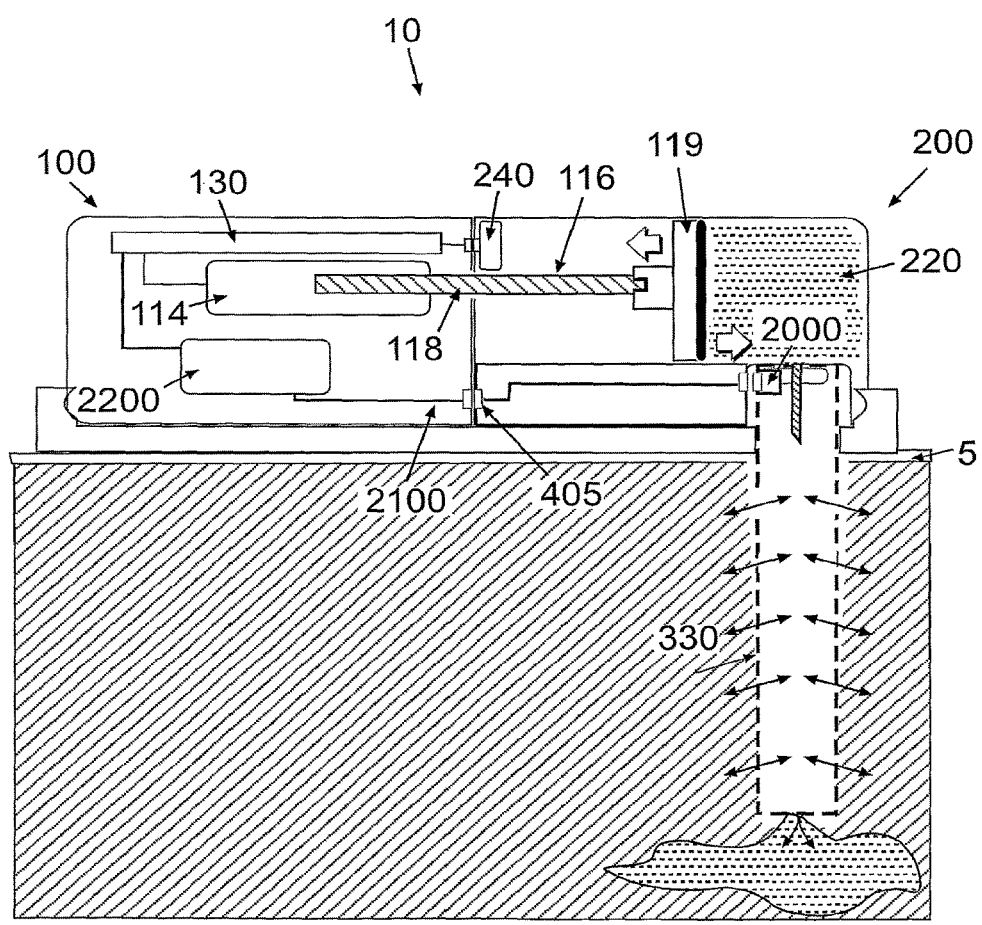

FIG. 26b shows an embodiment of a patch unit (10) that contains both dispensing and monitoring apparatuses. The monitoring apparatus contains extrinsic sensing means (2000) wired via connectors (410) to processor-controller (2200) connected to the electronics (130) residing in the reusable part (100). The dispensing apparatus employs, for example, a syringe type pumping mechanism (116). The driving mechanism (114) can push or pull the piston rod (118) which is paired with a plunger (119). Accordingly, flow can be delivered forward via the reservoir (220) in the disposable part (200) (from patch unit (10) to tip (330)) and backward (from tip (330) to patch unit (10)). Delivery of analyte-rich fluid from the distal end of the tip (330) to the proximal end within the patch unit (10) brings to the sensing means (2000) within the patch unit (10) a solution which contains analyte concentration identical (or at a known ratio) to that in the ISF.

Figure 27A:
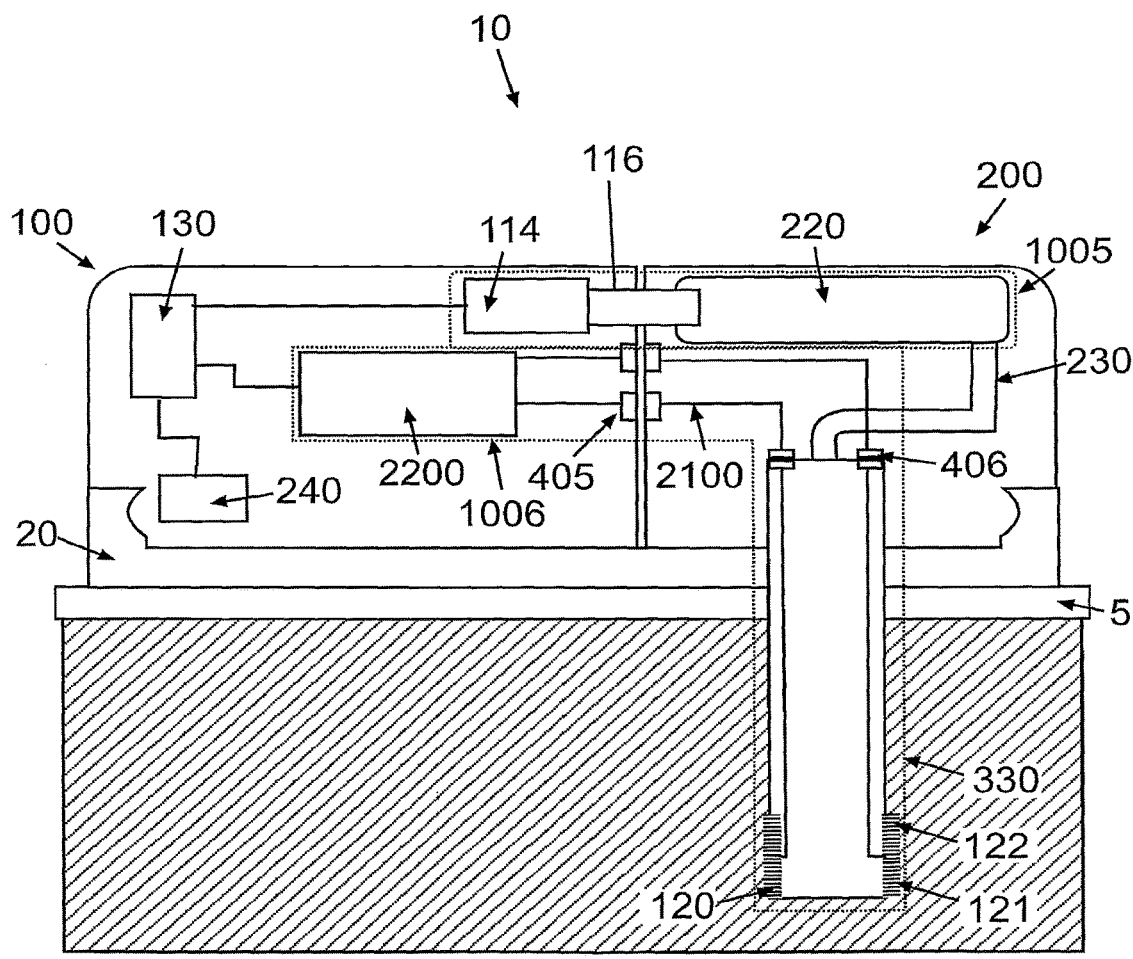
FIGS. 27a-b show an embodiment of a two-part patch unit employing an electrochemical monitoring mechanism and two embodiments of electrical current passage.
Figure 27B:
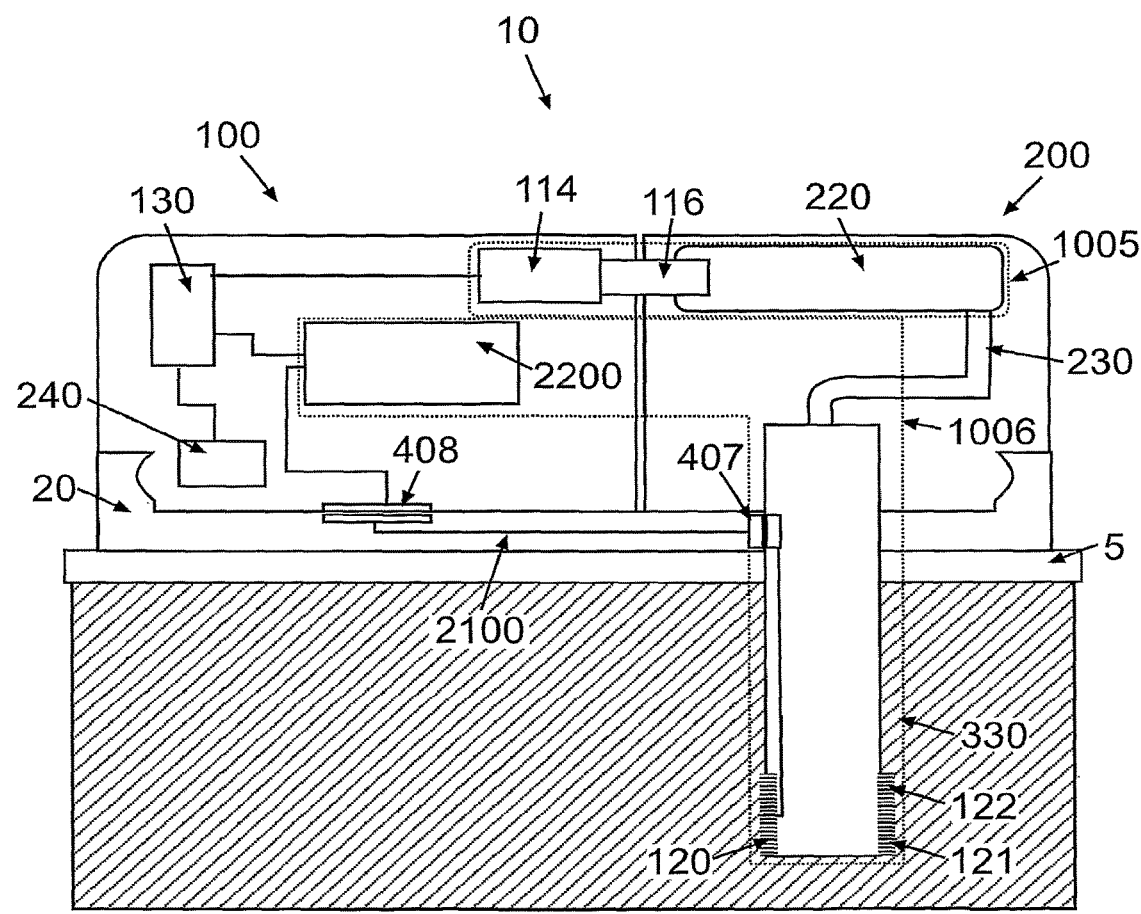

FIGS. 27a-b shows embodiments of the patch unit (10) having dispensing and monitoring apparatuses and configurations of electrical wires (2100). The monitoring apparatus (1006) includes intrinsic electrochemical sensing means. The dispensing apparatus (1005) includes electronics (130), processor-controller (2200), driving mechanism (114) and pumping mechanism (116), located in the reusable part (100), and reservoir (220) and delivery tube (230), located in the disposable part (200).

In FIG. 27a, electrical current generated on the electrodes (120, 121, 122) are delivered by wires (2100) to a set of contacts (406) at the proximal end of the tip (330). A set of contacts (405) transfer the electrical current from the disposable part (200) to the reusable part (100) and to the processor-controller (2200).

In FIG. 27b, electrical current generated on the electrodes (120, 121, and 122) are delivered by wires (2100) to a set of contacts (407) at the proximal end of the tip (330). An additional set of contacts (408) transfer the electrical current from the cradle unit (20) to the reusable part (100) and to the processor-controller (2200).

Figure 28:
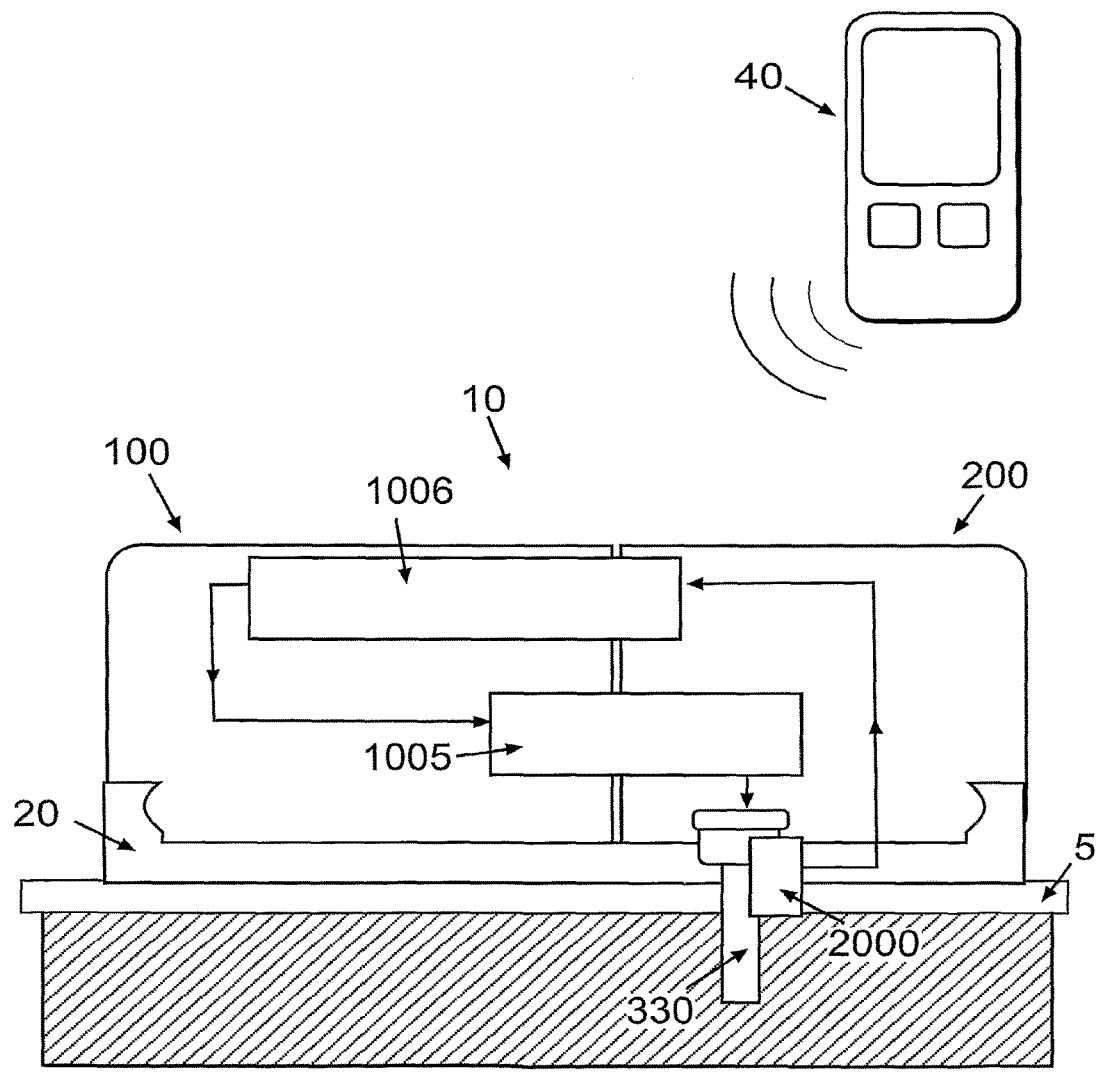
FIG. 28 shows an embodiment of a patch unit in which the monitoring and dispensing apparatuses work together as a closed loop or semi-closed loop system.

FIG. 28 shows one embodiment of the device that includes patch unit (10) and can include remote control unit (40). The patch unit (10) can be connected to cradle unit (20) and to tip (330). The patch unit (10) contains dispensing apparatus (1005) and monitoring apparatus (1006). The dispensing apparatus delivers fluid according to analyte concentration levels that are monitored by the monitoring apparatus (1006). The device can function as a closed loop or semi-closed loop system.

In some embodiments, insulin is dispensed according to bodily glucose levels and thus the system functions as closed loop system and is known in the art as an "artificial pancreas." In some embodiments, the patch unit (10) can include two parts—reusable part (100) and disposable part (200)—and can include buttons for inputting flow programs.

In the semi-closed loop system, additional inputs from the user (e.g., meal times, changes in basal insulin delivery rates, or boluses before meals) are used within a specific algorithm, to calculate the amount of insulin to be delivered by the dispensing apparatus (1005), as well as inputs from the monitoring apparatus (1006). User inputs can be done with the remote control unit (40) or with the buttons (not shown) on the patch unit (10).

In some embodiments, the patch unit (10) may be connected to a remote control unit (40) that controls the patch unit (10), where the remote control unit (40) further includes a blood glucose monitoring component that allows monitoring and controlling blood glucose levels in the body of the patient. Similar to the embodiments described above, the patch unit (10) may includea dual-purpose tip (330) and can be a one-part or a two-part patch unit. Further, the patch unit (10) may include the cradle unit (20), which can be adhered to the skin of the patient and accommodate insertion of the tip (330). In some embodiments, the patch unit (10) can be configured not to include the cradle unit (20).

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

Any patents, patent applications, articles and published and non-published documents referred to above are herein incorporated by reference in their entirety.

The invention claimed is:

1. A two-part patch unit comprising:
   a disposable part comprising:
      a first housing containing therewithin:
         a reservoir containing therapeutic fluid for delivery, and
         an energy supply; and
      a connecting lumen fluidly connected to the reservoir and fixed to the first housing; and
   a reusable part comprising a second housing containing therewithin:
      a driving mechanism;
      a monitoring apparatus for monitoring an analyte level and comprising an electrochemical sensing mechanism; and
      a processor-controller; and
   a cradle unit comprising:
      a first surface receiving the disposable part and the reusable part;
      a second surface comprising an adhesive for coupling to a skin surface; and
      a well defining an opening between the first and second surfaces;
   a cannula comprising:
      an outer periphery along a longitudinal length which extends down from the second surface of the cradle unit; and
      an open end distal from a proximal end adjacent to the reusable part and the disposable part;
   a self-sealable septum coupled to the proximal end of the cannula, the reservoir being fluidically connectable to the cannula through the self-sealable septum via the connecting lumen which is configured to pierce the septum directly and immediately upon connection of the disposable part and reusable part to the cradle unit to deliver the therapeutic fluid out the open end, the cannula and septum are insertable together into the well with the cradle unit coupled to the skin surface, and wherein the well of the cradle anchors the septum and cannula upon insertion therein; and
   a plurality of electrodes coupled to the outer periphery adjacent the open end of the cannula.

2. The two-part patch unit of claim 1 wherein the energy supply comprises one or more batteries within the disposable part.

3. The two-part patch unit of claim 1 wherein the cannula is configured to function as a probe for monitoring the analyte level within an interstitial fluid via the plurality of electrodes and at the same time is configured for delivery of the therapeutic fluid from the reservoir to a site under the skin surface.

4. The two-part patch unit of claim 1 further comprising a penetrating member comprising a sharpened piece used for pricking of the skin during cannula insertion, and that is removable upon insertion of the cannula through the skin surface.

5. The two-part patch unit of claim 1 wherein the cannula is a soft cannula.

6. The two-part patch unit of claim 1 further comprising an outlet port through which the therapeutic fluid passes in moving out of the reservoir for the delivery under the skin surface.

7. The two-part patch unit of claim 1 wherein the cannula comprises a substantially circular cross-sectional shape.

8. The two-part patch unit of claim 1 wherein the cannula extends through the cradle unit via the well, the well comprising protrusions extending upwardly away from the skin surface for anchoring the cannula to the cradle unit.

9. The two-part patch unit of claim 1 wherein the plurality of electrodes comprise concentric, ring-like, electrodes located transversally on the outer periphery of the cannula and each is separated from one another along the longitudinal length of the cannula.

10. The two-part patch unit of claim 1 wherein the plurality of electrodes comprises a working electrode, a counter electrode and a reference electrode.

11. The two-part patch unit of claim 10 wherein the working electrode comprises an enzyme-coated sensing layer.

12. The two-part patch unit of claim 1 further comprising connectors that close the electrical circuit after coupling with the disposable part such that upon such coupling, power is supplied to the reusable part via one or more batteries within the disposable part.

13. The two-part patch unit of claim 1 wherein the opening of the well between the first and second surfaces is bigger on the second surface than on the first surface.

14. The two-part patch unit of claim 1 wherein the disposable part and the reusable part each contact the first surface.

15. The two-part patch unit of claim 1 wherein the opening of the well between the first and second surfaces is bigger on the second surface than on the first surface, and the disposable part and the reusable part each contact the first surface.

16. A method of using a two-part patch unit comprising: providing the two-part patch unit comprising:
   a disposable part comprising:
     a first housing containing therewithin:
       a reservoir containing therapeutic fluid for delivery, and
       an energy supply; and
       a connecting lumen fluidly connected to the reservoir and fixed to the first housing; and
   a reusable part comprising a second housing containing therewithin:
     a driving mechanism;
     a monitoring apparatus for monitoring an analyte level and comprising an electrochemical sensing mechanism; and
     a processor-controller; and
   a cradle unit comprising:
     a first surface receiving the disposable part and the reusable part;
     a second surface comprising an adhesive for coupling to a skin surface; and
     a well defining an opening between the first and second surfaces; and
   a cannula comprising:
     an outer periphery along a longitudinal length which extends down from the second surface of the cradle unit; and
     an open end distal from a proximal end adjacent to the reusable part and the disposable part;
   a self-sealable septum coupled to the proximal end of the cannula, the reservoir being fluidically connectable to the cannula through the self-sealable septum via the connecting lumen which is configured to pierce the septum directly and immediately upon connection of the disposable part and reusable part to the cradle unit to deliver the therapeutic fluid out the open end, the cannula and septum are insertable together into the well with the cradle unit coupled to the skin surface, and wherein the well of the cradle anchors the septum and cannula upon insertion therein; and
   a plurality of electrodes coupled to the outer periphery adjacent the open end of the cannula; and
   coupling the cradle unit to the skin surface; and
   monitoring the analyte level within an interstitial fluid via the plurality of electrodes on the cannula and at the same time delivering fluid from the reservoir to a site under the skin surface via the cannula of the two-part patch unit.

17. The method of claim 16 wherein the plurality of electrodes comprises concentric, ring-like, electrodes located transversally on the outer periphery of the cannula and each is separated from one another along the longitudinal length of the cannula.

18. The method of claim 16 wherein the plurality of electrodes comprises a working electrode, a counter electrode and a reference electrode.

19. The method of claim 18 further comprising sensing, via an enzyme-coated sensing layer on the working electrode, a glucose level in the interstitial fluid.

20. The method of claim 19 further comprising continuously sensing the glucose.

* * * * *